United States Patent [19]
Hart

[11] Patent Number: 5,407,917
[45] Date of Patent: Apr. 18, 1995

[54] COMPOSITIONS AND METHODS FOR THE ENHANCEMENT OF PERFORMANCE IN MEAT-PRODUCING ANIMALS AND FOR THE TREATMENT AND CONTROL OF DISEASE THEREIN

[75] Inventor: Ian C. Hart, Pennington, N.J.

[73] Assignee: American Cyanamid Company, Wayne, N.J.

[21] Appl. No.: 142,546

[22] Filed: Oct. 22, 1993

Related U.S. Application Data

[63] Continuation of Ser. No. 756,938, Sep. 9, 1991, abandoned.

[51] Int. Cl.$^6$ .............................................. A61K 31/70
[52] U.S. Cl. ....................................................... 514/25
[58] Field of Search .......................................... 514/25

[56] References Cited

U.S. PATENT DOCUMENTS

| | | | |
|---|---|---|---|
| 4,704,276 | 11/1987 | Kantor | 424/122 |
| 4,705,688 | 11/1987 | Carter et al. | 424/122 |
| 4,753,798 | 6/1988 | Kantor et al. | 424/122 |
| 4,968,493 | 11/1990 | Carter et al. | 424/122 |

*Primary Examiner*—Jerome D. Goldberg
*Attorney, Agent, or Firm*—Thomas S. Szatkowski

[57] ABSTRACT

Methods for increasing the growth rate and increasing the efficiency of food utilization of meat-producing animals and for treating bacterial infections in said animals by administering an effective amount of selected antibiotics derived from the microorganism *Streptomyces lydicus* ssp. *tanzanius* (NRRL 18036) are described herein.

5 Claims, 24 Drawing Sheets

FIG. 3  PROTON NUCLEAR MAGNETIC RESONANCE SPECTRUM OF LL-E19020 α IN CDCL$_3$ SOLUTION

CARBON-13 NUCLEAR MAGNETIC RESONANCE SPECTRUM OF LL-E19020 α IN CDCL₃ SOLUTION

FIG. 7  PROTON NUCLEAR MAGNETIC RESONANCE SPECTRUM OF LL-E19020 α. IN CDCL₃ SOLUTION

FIG. 11 PROTON NUCLEAR IN CDCL SOLUTION OF LL-E19020E psilon

FIG. 12 CARBON-13 NUCLEAR MAGNETIC RESONANCE SPECTRUM OF LL-E1902E IN CDCL$_3$ SOLUTION

FIG. 15 PROTON NUCLEAR MAGNETIC RESONANCE SPECTRUM OF LL-E19020E, IN ACETONE d6 SOLUTION

FIG. 16　CARBON-13 NUCLEAR MAGNETIC RESONANCE SPECTRUM OF LL-E1902E IN ACETONE d6 SOLUTION

FIG. 19 PROTON NUCLEAR MAGNETIC RESONANCE SPECTRUM OF LL-E19020E α IN CDCl$_3$ SOLUTION

PROTON NUCLEAR MAGNETIC RESONANCE SPECTRUM OF LL-E19020E α IN CDCL₃ SOLUTION

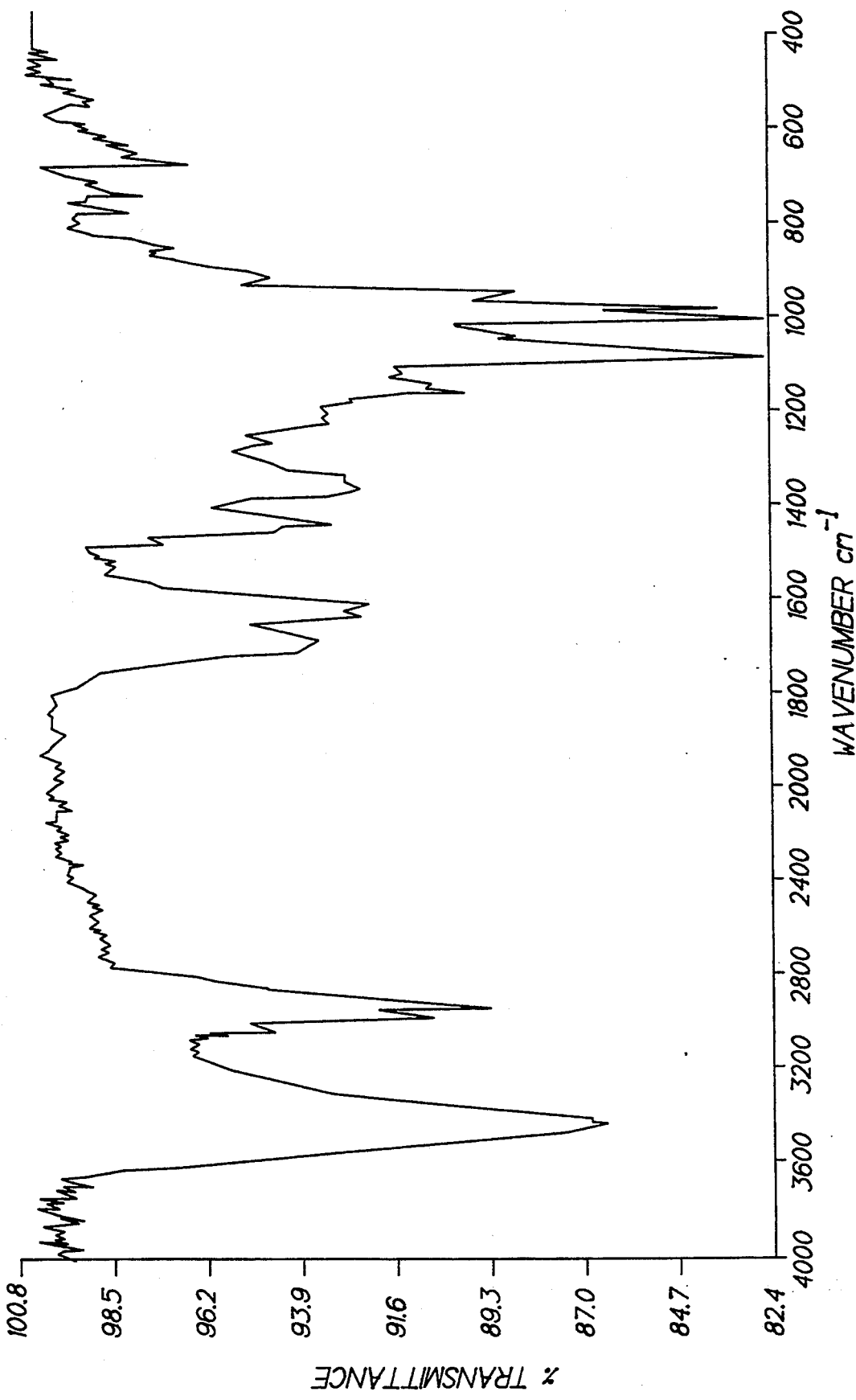

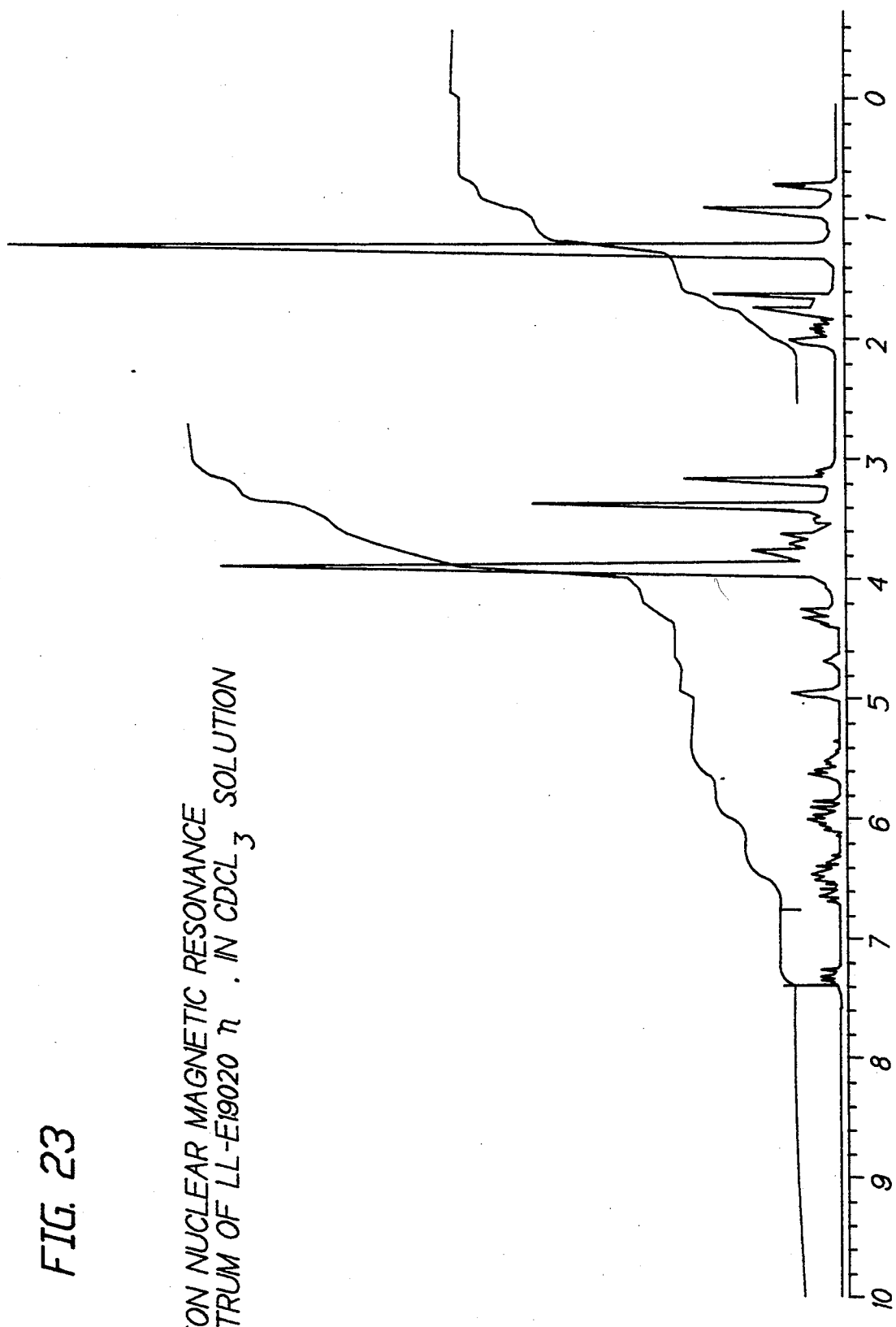
FIG. 23 PROTON NUCLEAR MAGNETIC RESONANCE SPECTRUM OF LL-E19020 η . IN $CDCL_3$ SOLUTION

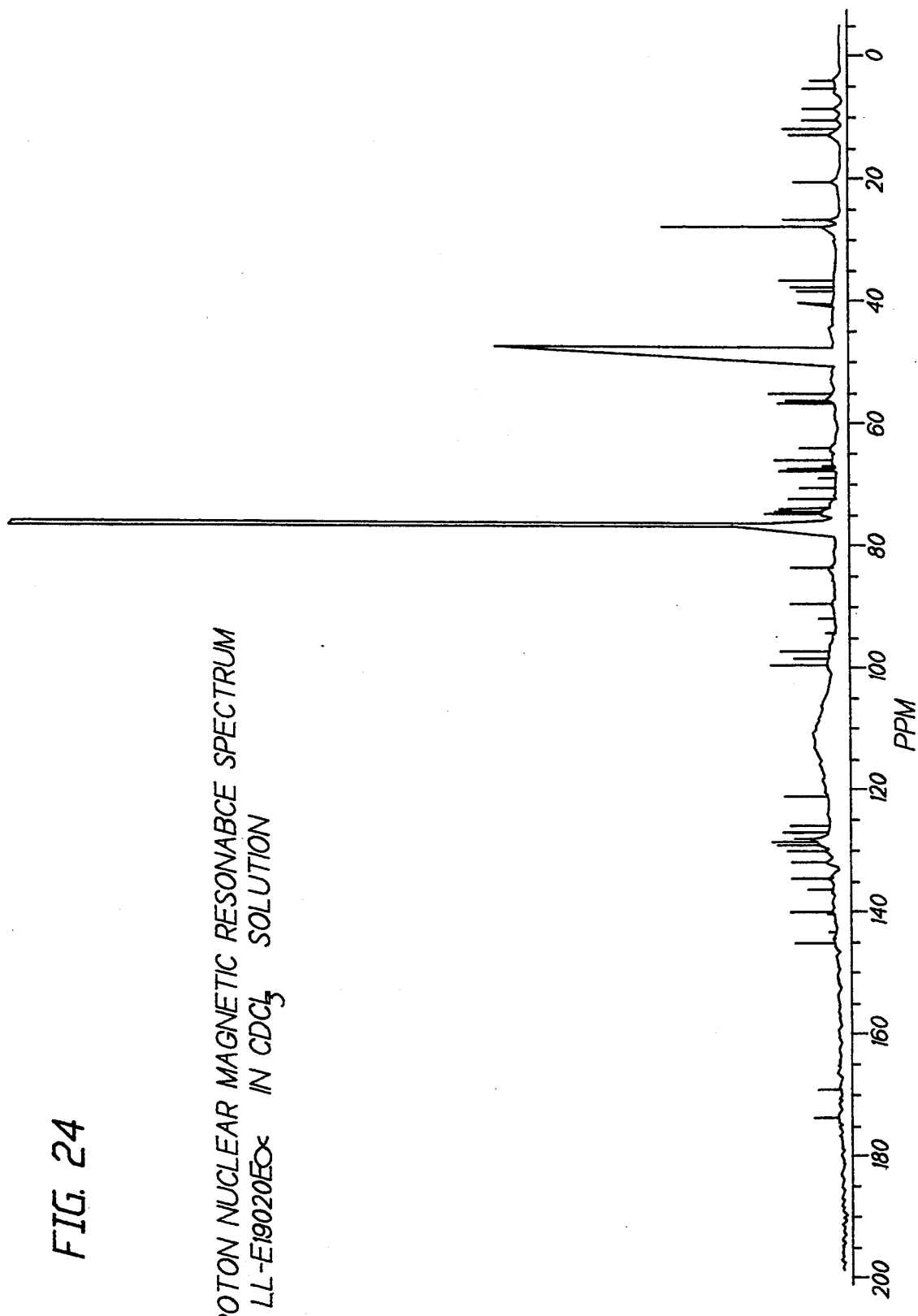
FIG. 24 PROTON NUCLEAR MAGNETIC RESONANCE SPECTRUM OF LL-E19020Eα IN CDCl₃ SOLUTION

COMPOSITIONS AND METHODS FOR THE ENHANCEMENT OF PERFORMANCE IN MEAT-PRODUCING ANIMALS AND FOR THE TREATMENT AND CONTROL OF DISEASE THEREIN

This is a continuation of application Ser. No. 07/756,938 filed on Sep. 9, 1991, now abandoned.

BACKGROUND OF THE INVENTION

In order to meet the needs of an ever-increasing human population, livestock producers continually seek efficient and effective means of enhancing the production of fiber, meat, milk and eggs. Further, agronomists must constantly find ways to combat the undesirable effects of disease inherent in breeding and raising livestock.

Importantly, it has been recognized by the livestock industry that there is currently no entirely satisfactory method for preventing, treating or controlling bacterial infection in livestock or domestic animals.

Antibiotics LL-E19020α and LL-E19020β are described in U.S. Pat. No. 4,705,668 and their use in warm-blooded animals is described in U.S. Pat. Nos. 4,704,276, 4,753,798 and 4,968,493.

It is an object of the present invention to provide methods and composition for increasing the growth rate of meat-producing animals and improving the efficiency of feed utilization thereby.

It is a further object of this invention to provide a method and composition for preventing, ameliorating or controlling bacterial disease in meant-producing and companion animals.

More particularly, it is also an object of this invention to provide a method and composition for preventing, ameliorating or controlling necrotic enteritis in poultry and dysentery in swine.

SUMMARY OF THE INVENTION

The present invention relates to a method for increasing the growth rate of meat-producing animals and fish and for increasing the efficiency of feed utilization thereby by administering to the animals or fish an effective amount of an antibiotic selected from the, group consisting of LL-E19020 gamma, LL-E119020 epsilon, LL-E19020 epsilon$_1$, LL-E19020 alpha$_1$, LL-E19020 zeta, L1-E19020 eta and the pharmacologically acceptable salts thereof.

This invention also relates to a method for preventing, ameliorating or controlling bacterial infections in warm-blooded animals by administering to the animals a therapeutically effective amount of an antibiotic selected from the group consisting of LL-E19020 gamma, LL-E119020 epsilon, LL-E19020 epsilon$_1$, LL-E19020 alpha$_1$, LL-E19020 zeta, L1-E19020 eta and the pharmacologically suitable salts thereof.

The present invention further relates to animal feed compositions suitable for oral administration and effective for the enhancement of performance in meat-producing animals and fish and for the prevention and control of bacterial infection in meat-producing and companion animals.

The antibiotic compounds which are effective when used in the compositions and methods of the present invention are derived from the microorganism *Streptomyces lydicus* subspecies tanzanius (NRRL 18036) and are designated LL-E19020γ (gamma), LL-E19020ε (epsilon), LL-E19020ε$_1$ (epsilon$_1$), LL-E19020α$_1$ (alpha$_1$) LL-E19020ζ (zeta) and LL-E19020η (eta). These antibiotic compounds and methods for the preparation thereof are described in co-pending patent application Ser. Nos. 07/756,411, 07/756,931, 07/756,646, and 07/756,406, respectively, filed concurrently herewith and incorporated herein by reference thereto.

Also effective for use in the compositions and methods of the present invention are the pharmacologically suitable salts of antibiotics LL-E19020γ, LL-E19020ε, LL-E19020ε$_1$ and LL-E19020α$_1$, LL-E19020ζ and LL-E19020η.

BRIEF DESCRIPTION OF THE DRAWINGS

FIG. I shows the ultraviolet absorption spectrum of LL-E19020 Gamma.

FIG. II shows the infrared absorption spectrum of LL-E19020 Gamma.

Figure 1:
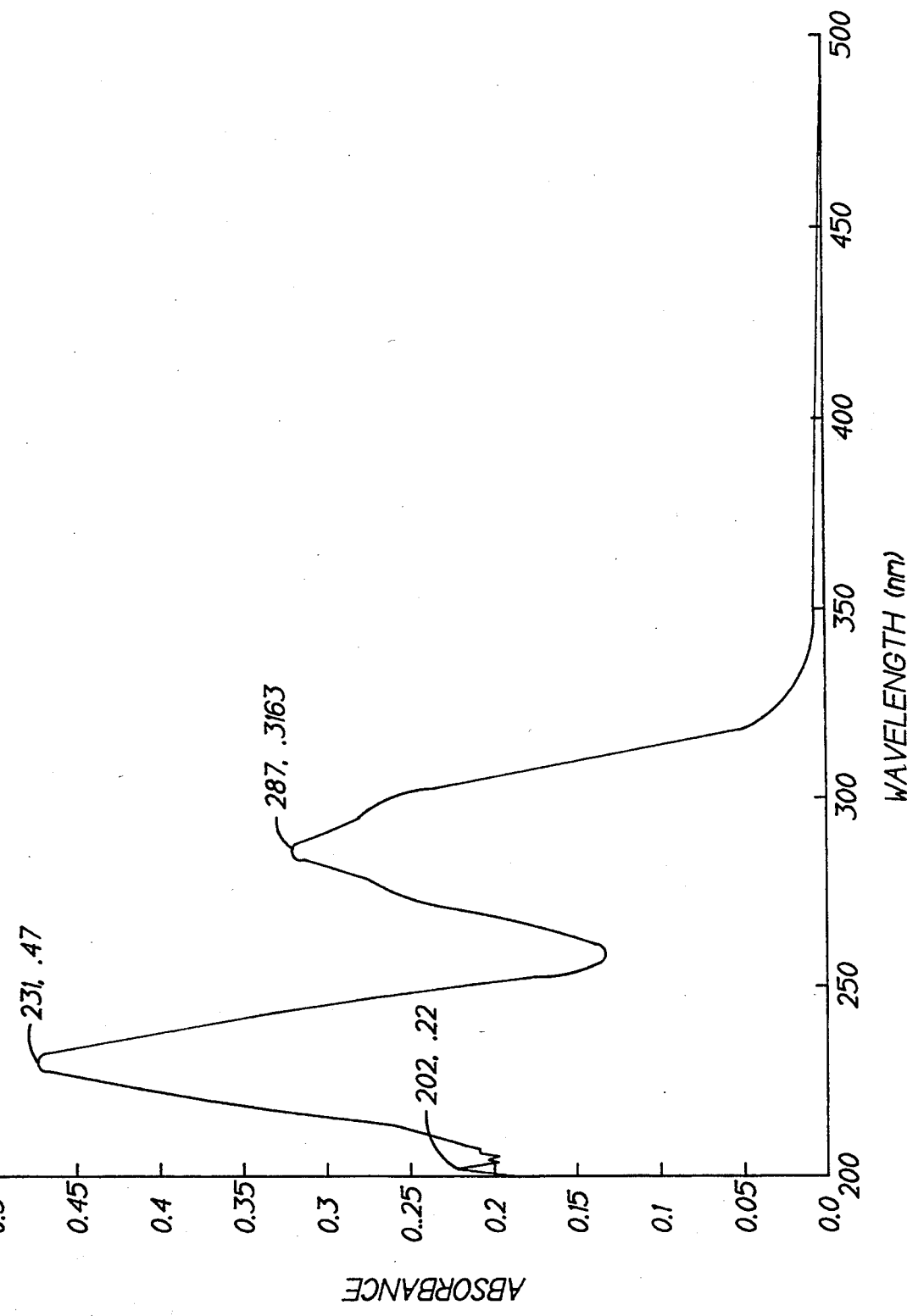
Figure 2:
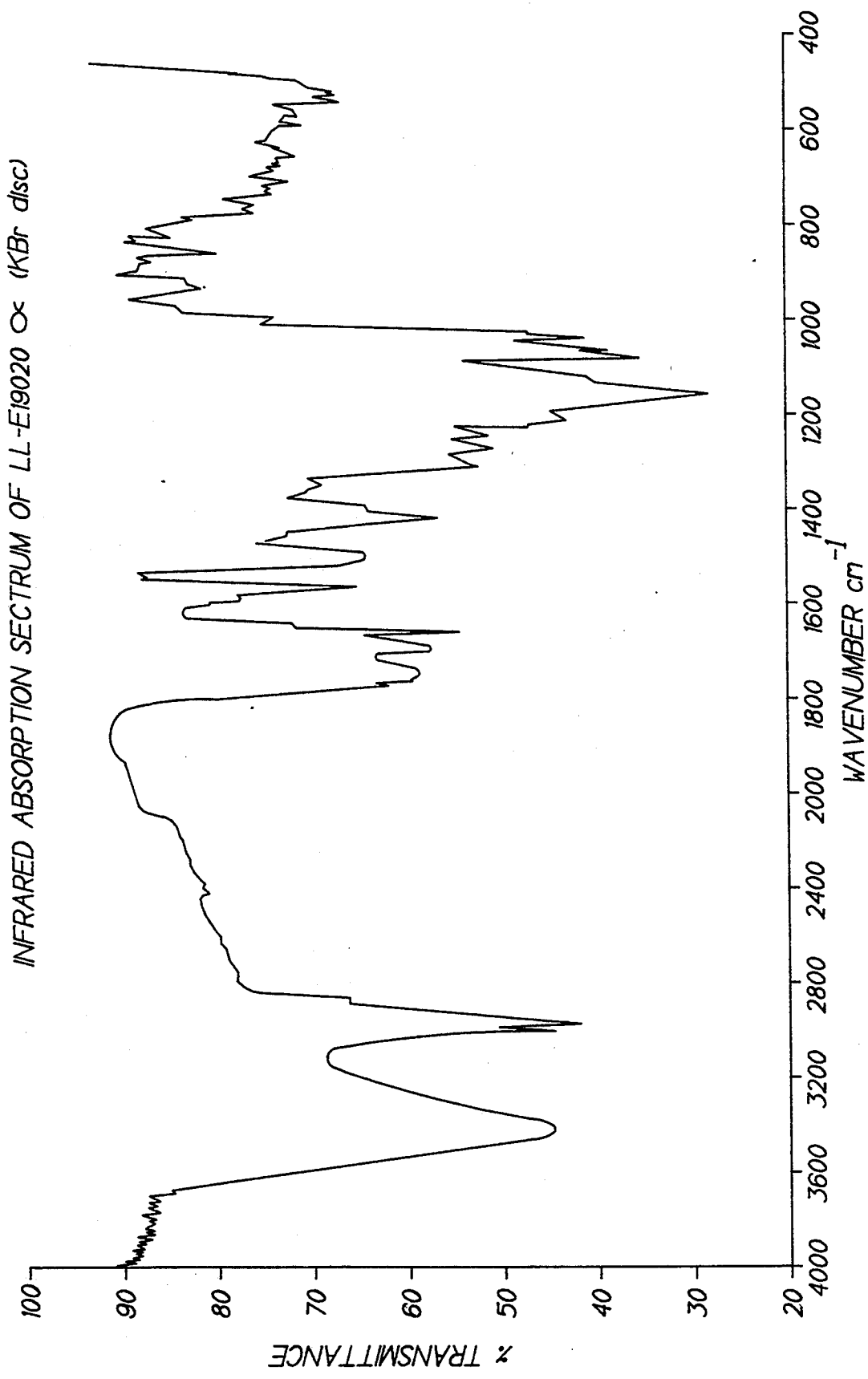
Figure 3:
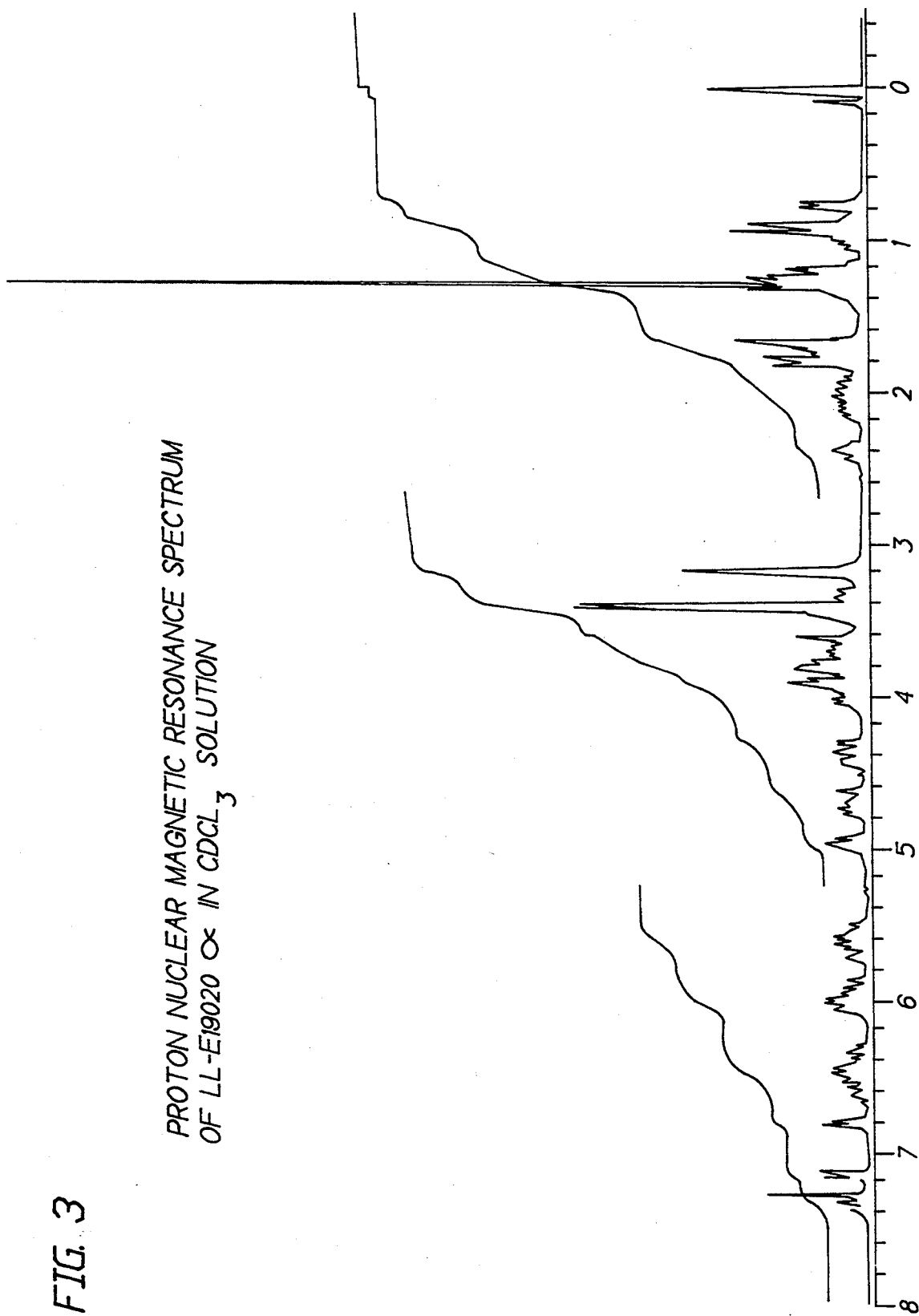
Figure 4:
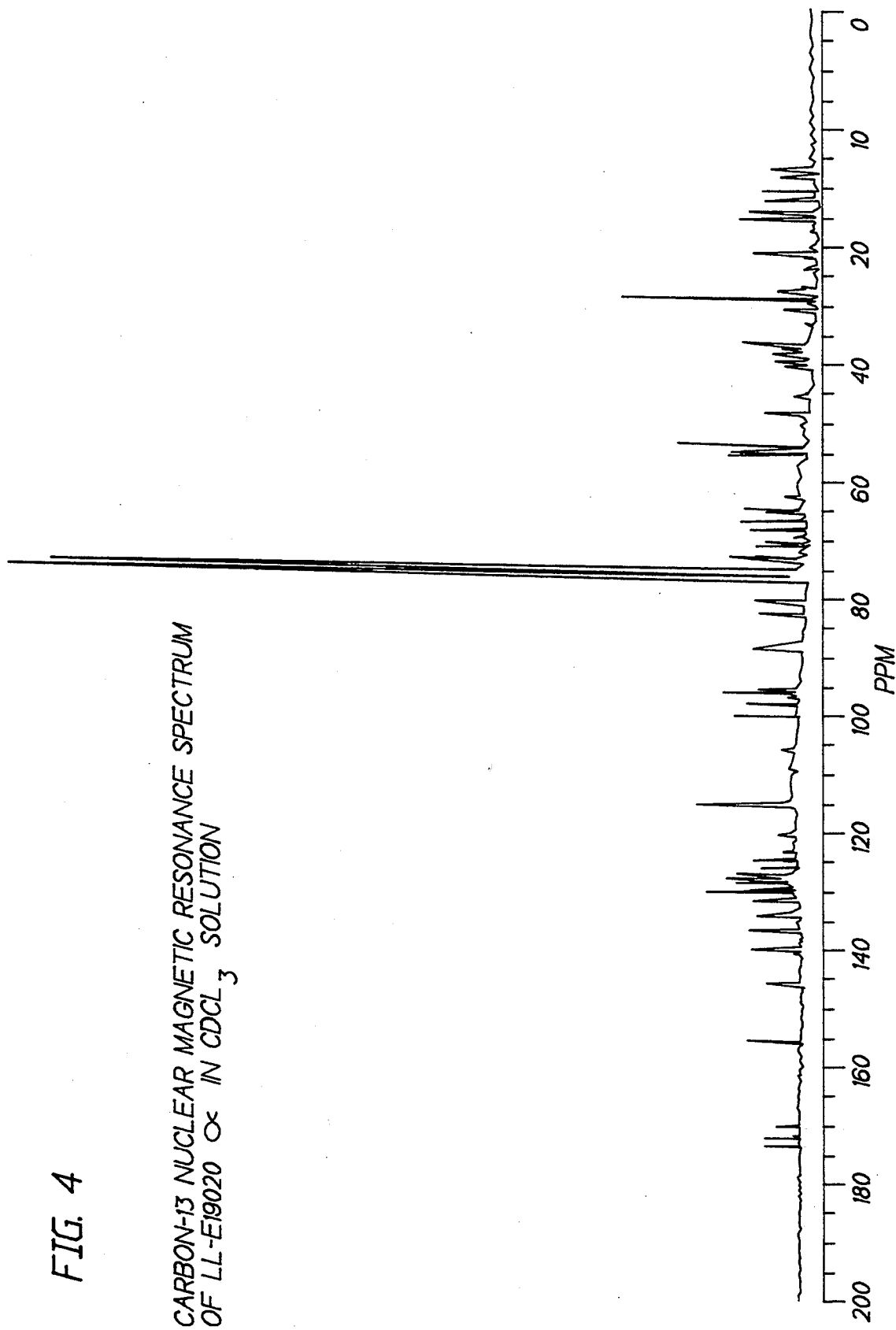
Figure 5:
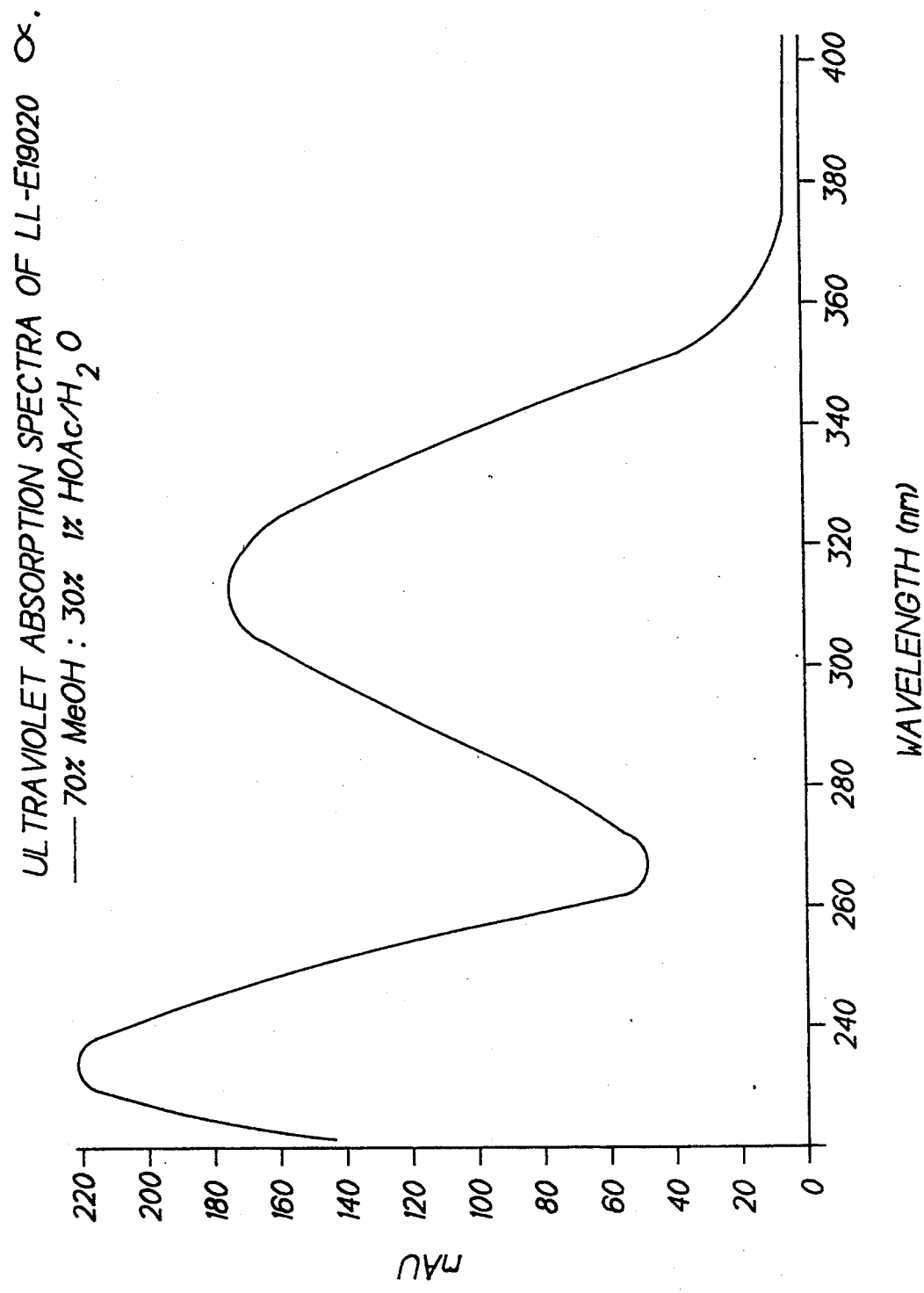
Figure 6:
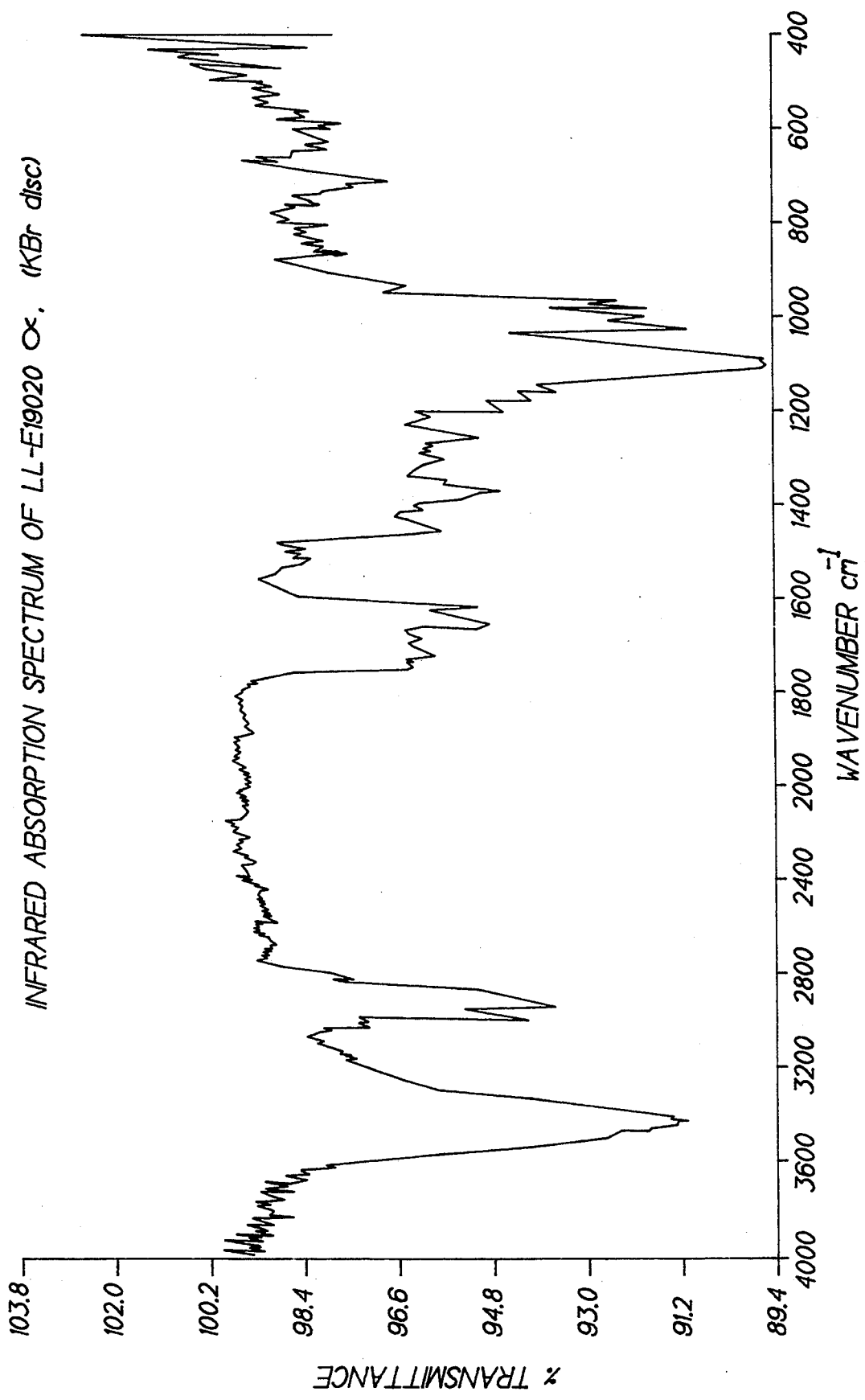
Figure 7:
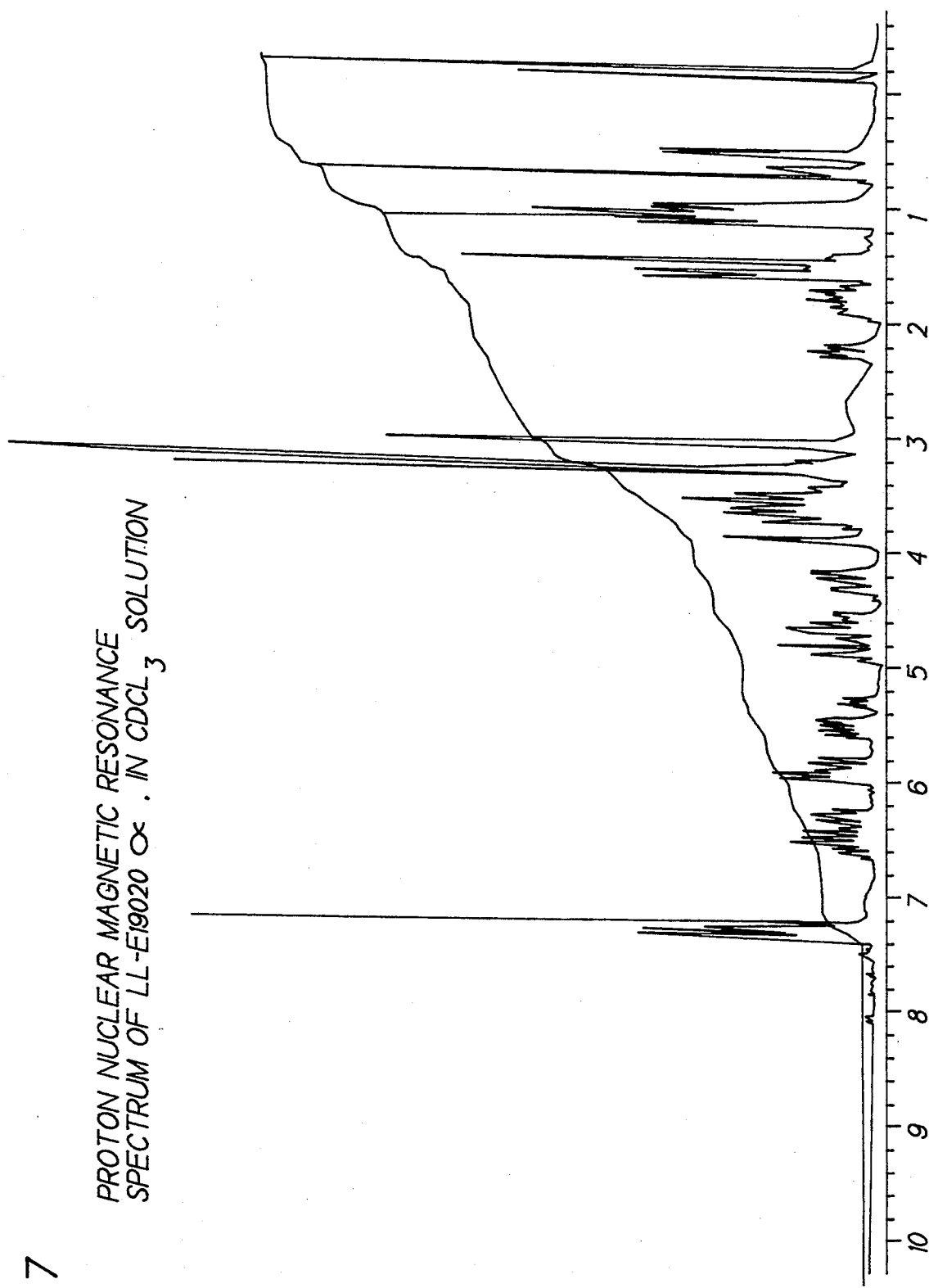
Figure 8:
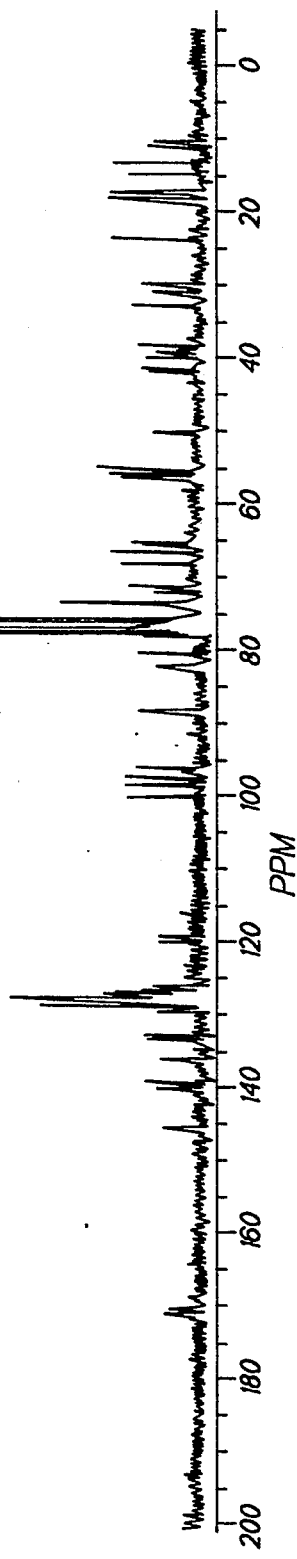
Figure 9:
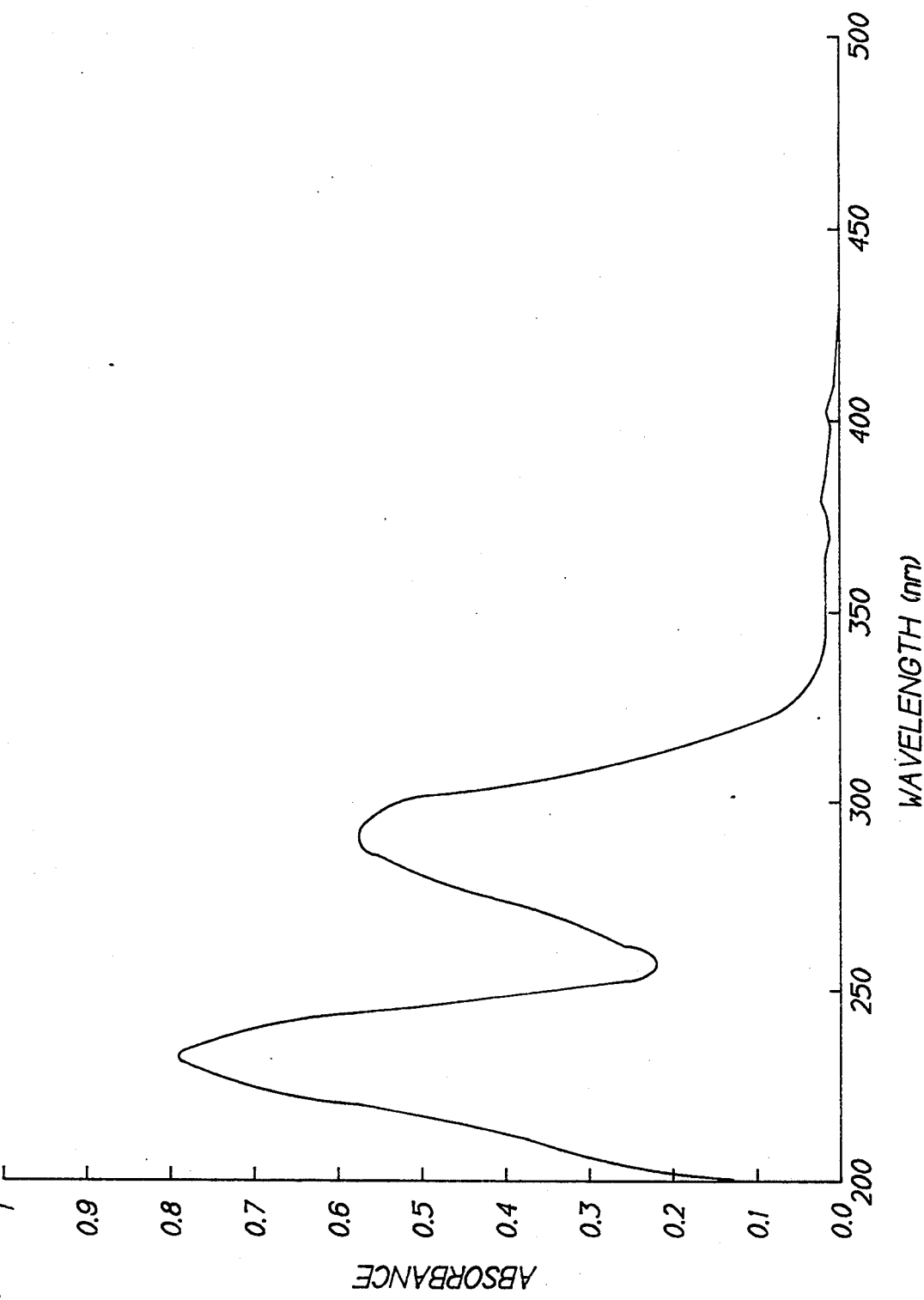
Figure 10:
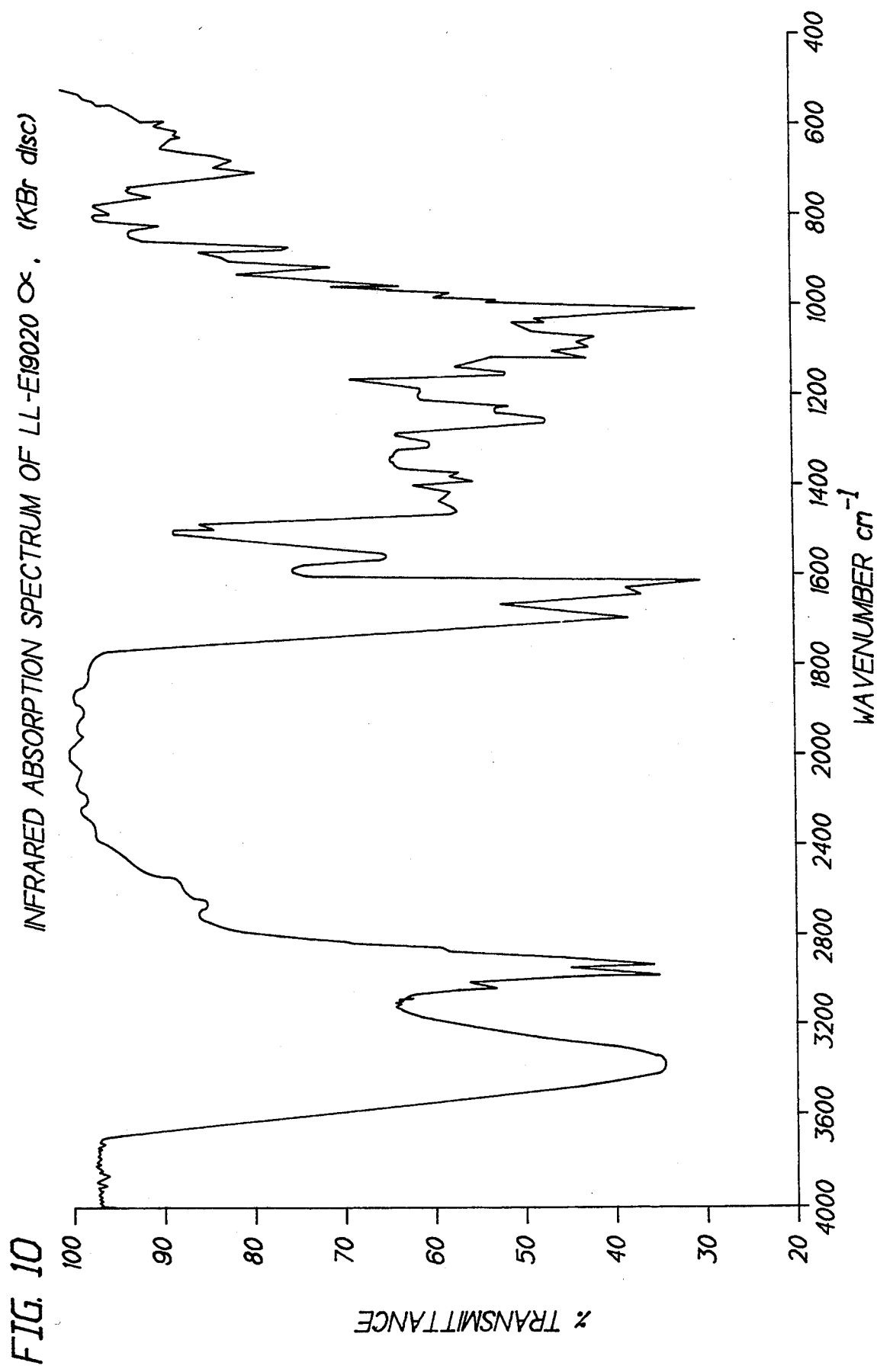
Figure 11:
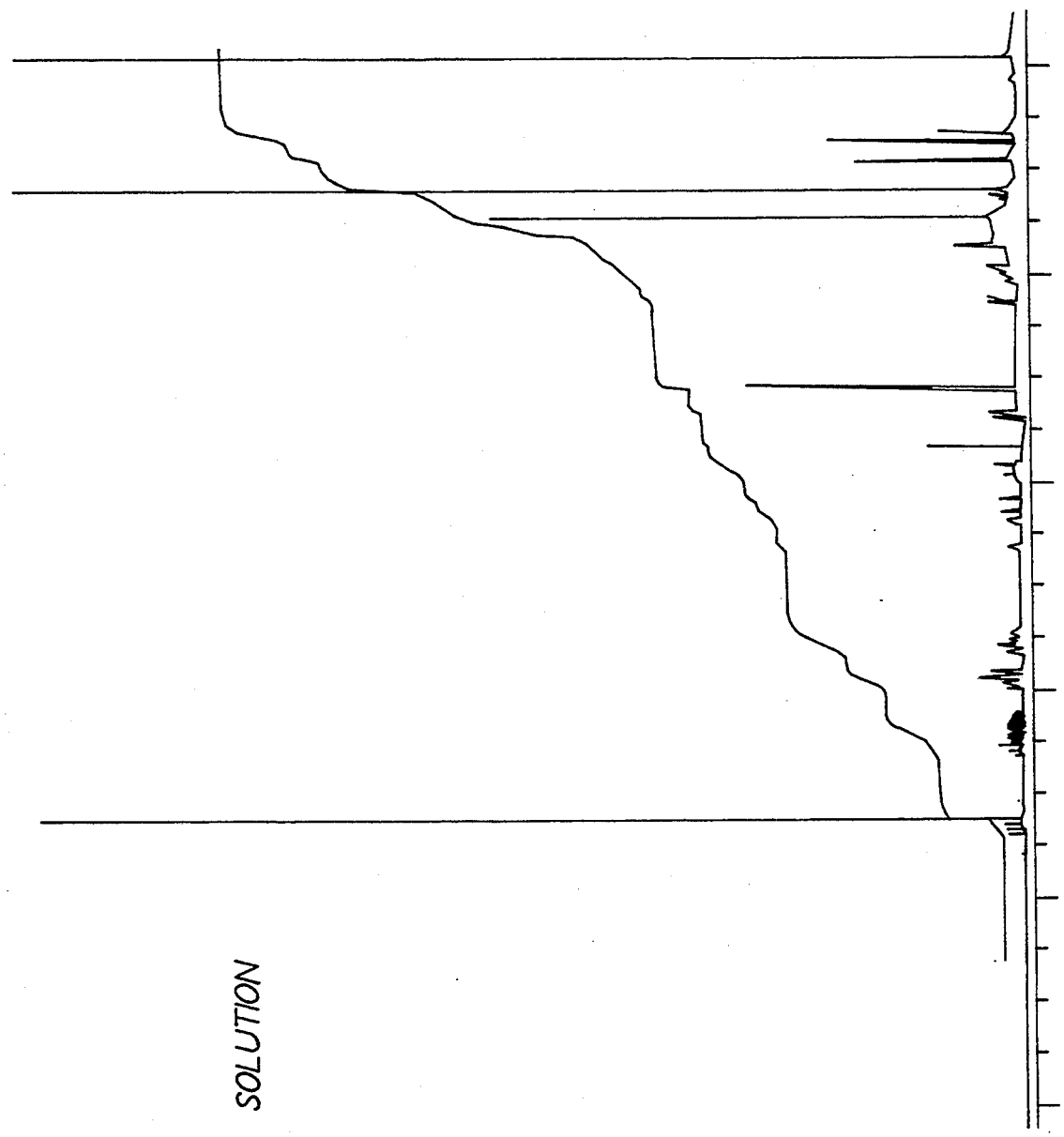
Figure 12:
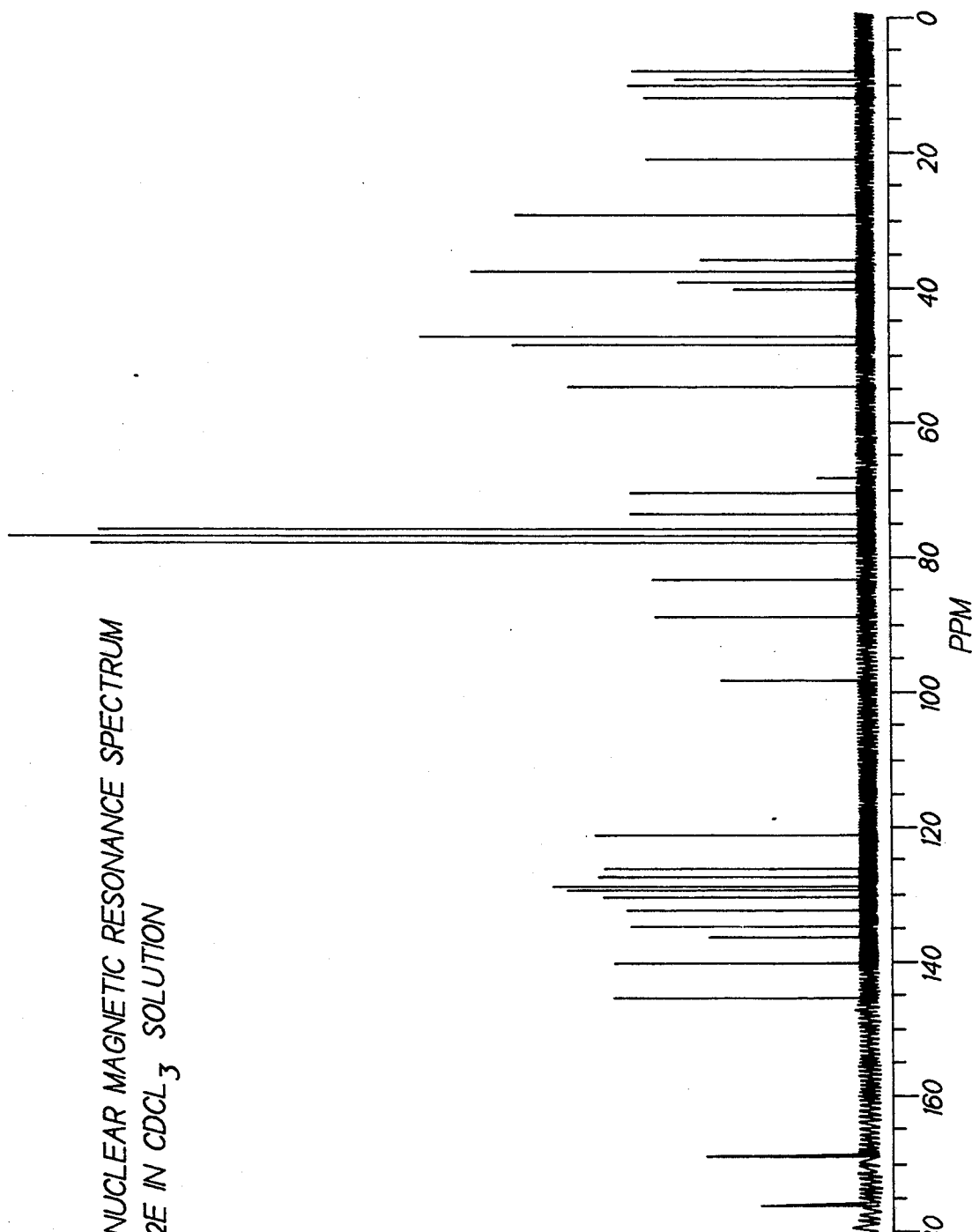
Figure 13:
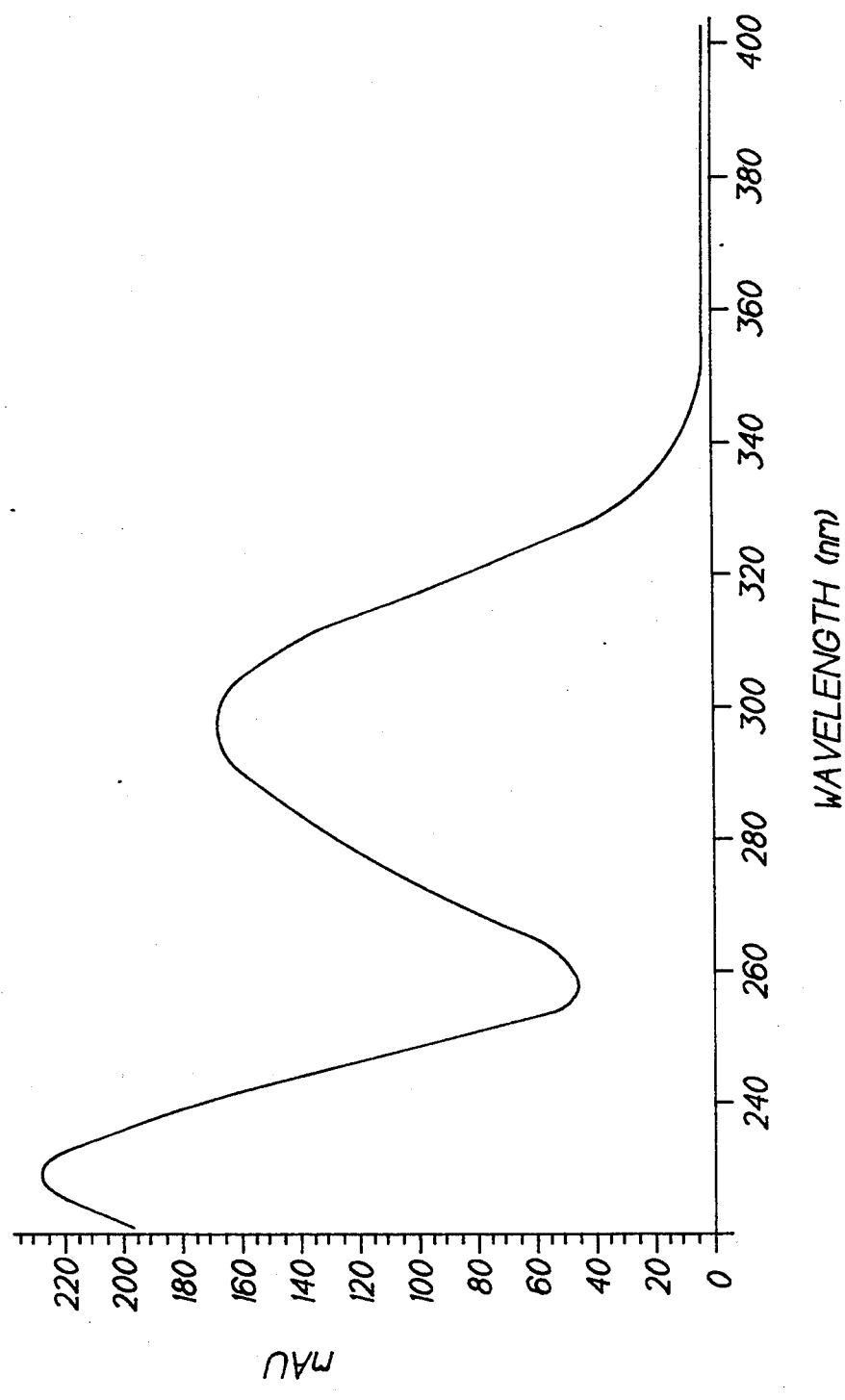
Figure 14:
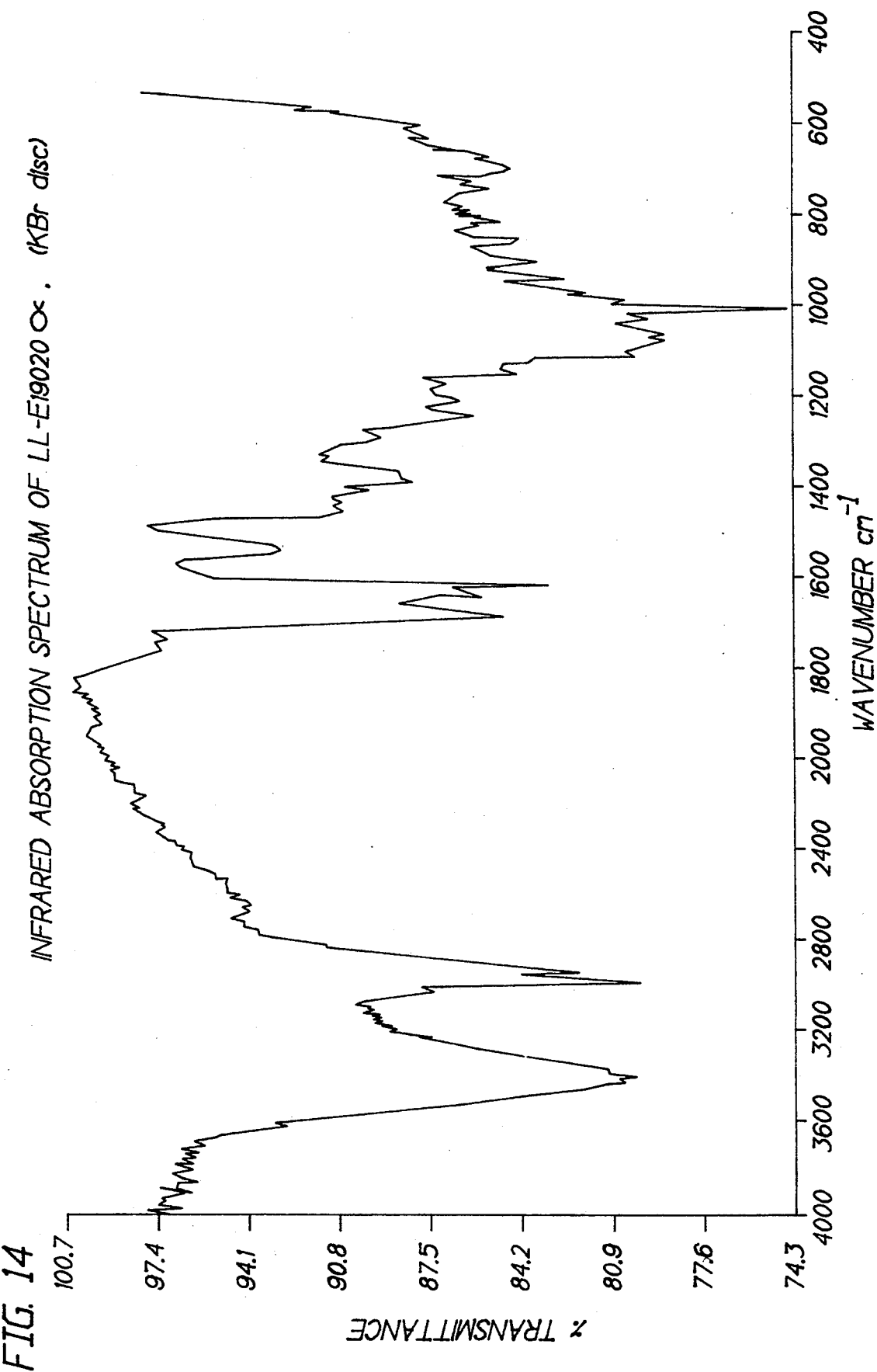
Figure 15:
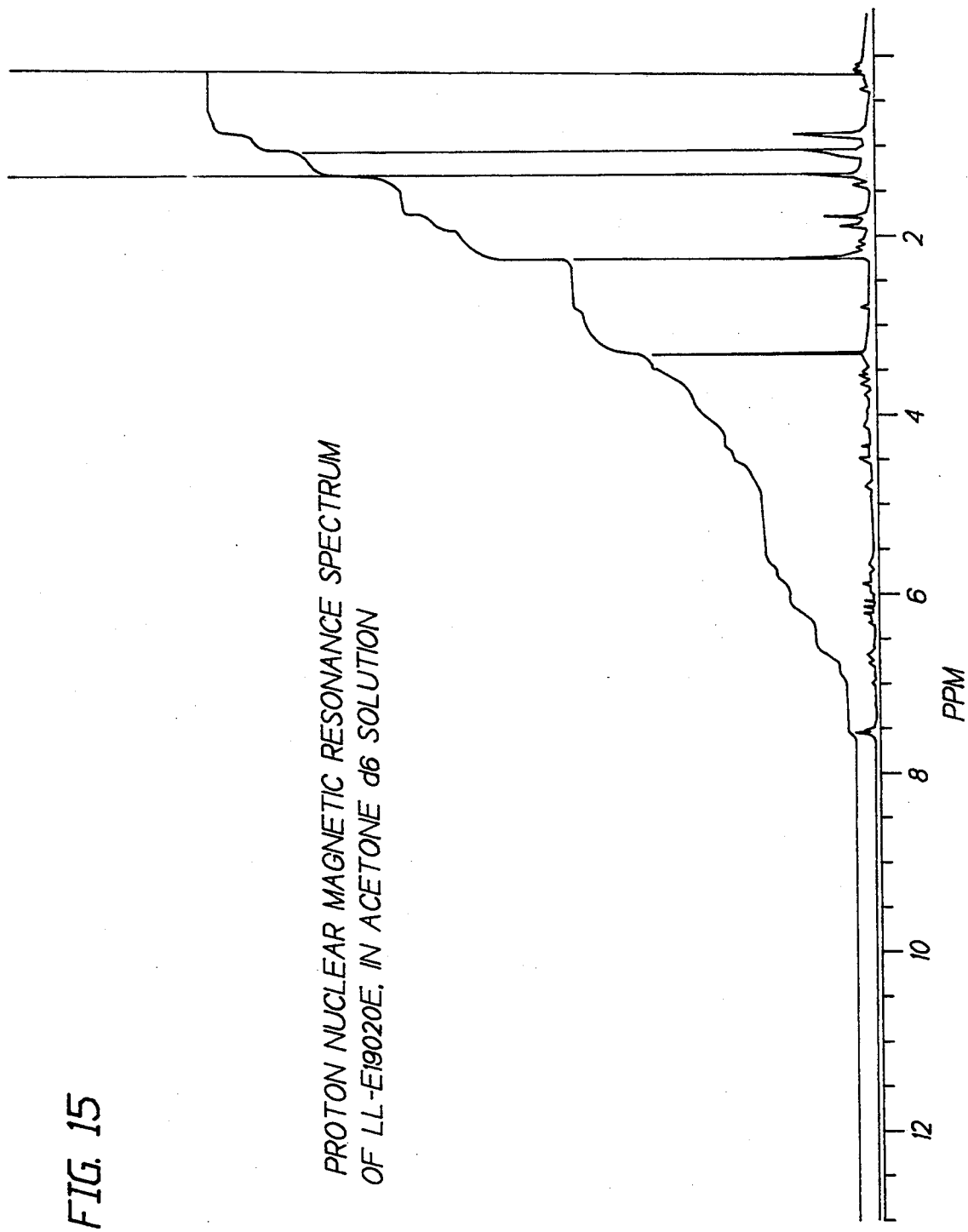
Figure 16:
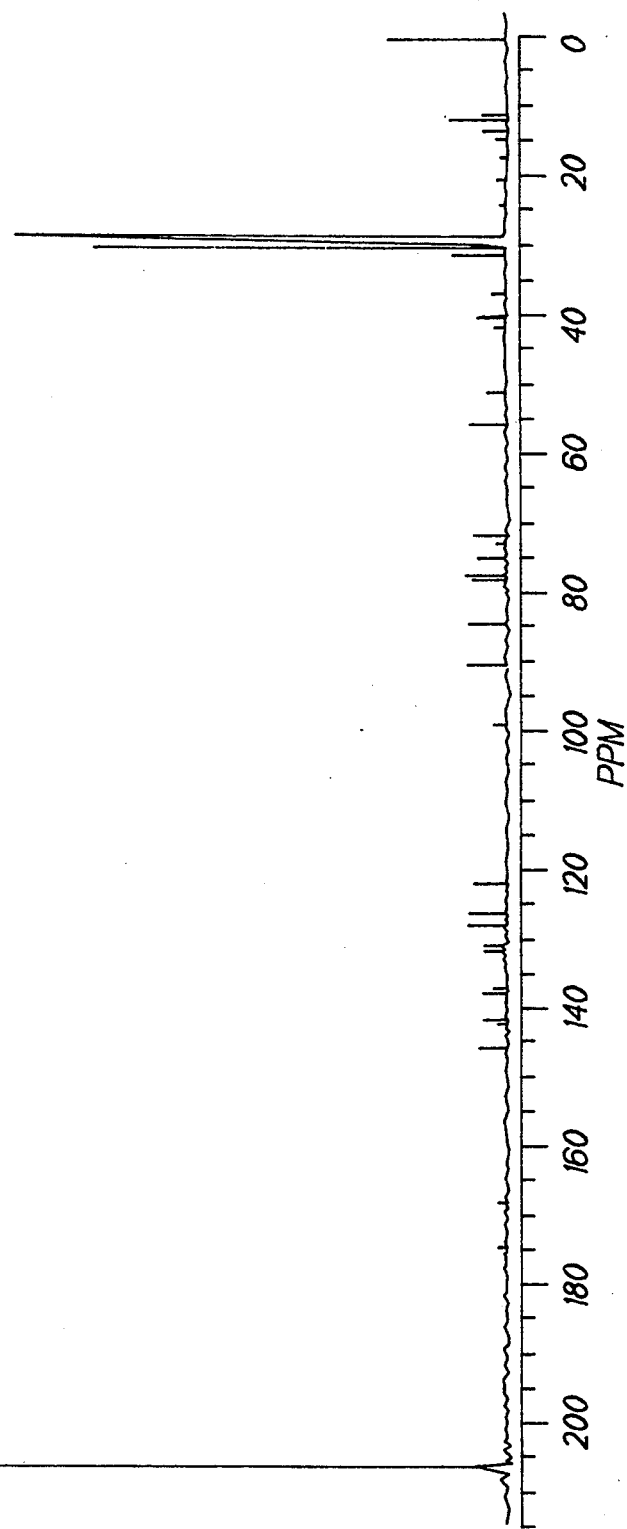
Figure 17:
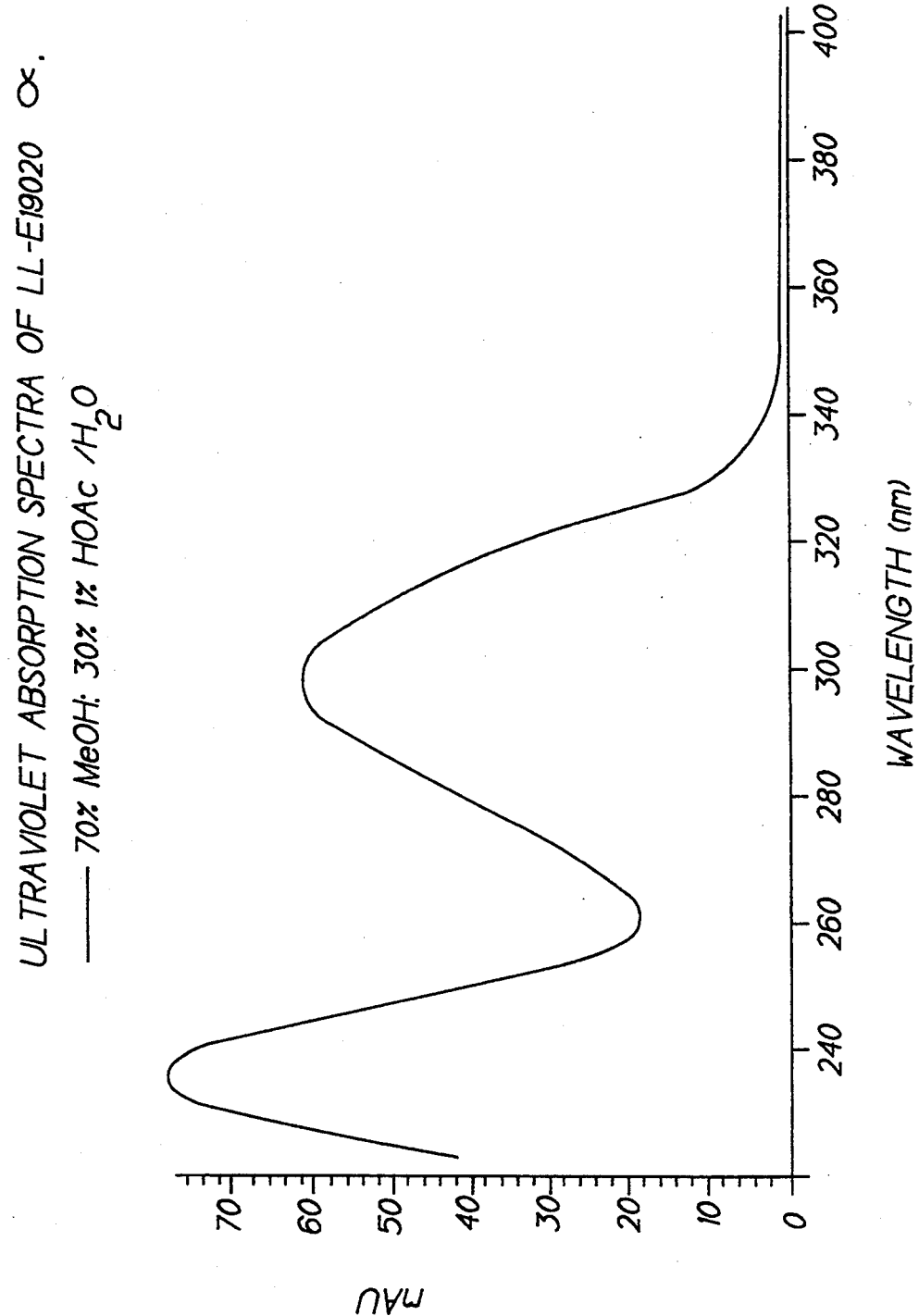
Figure 18:
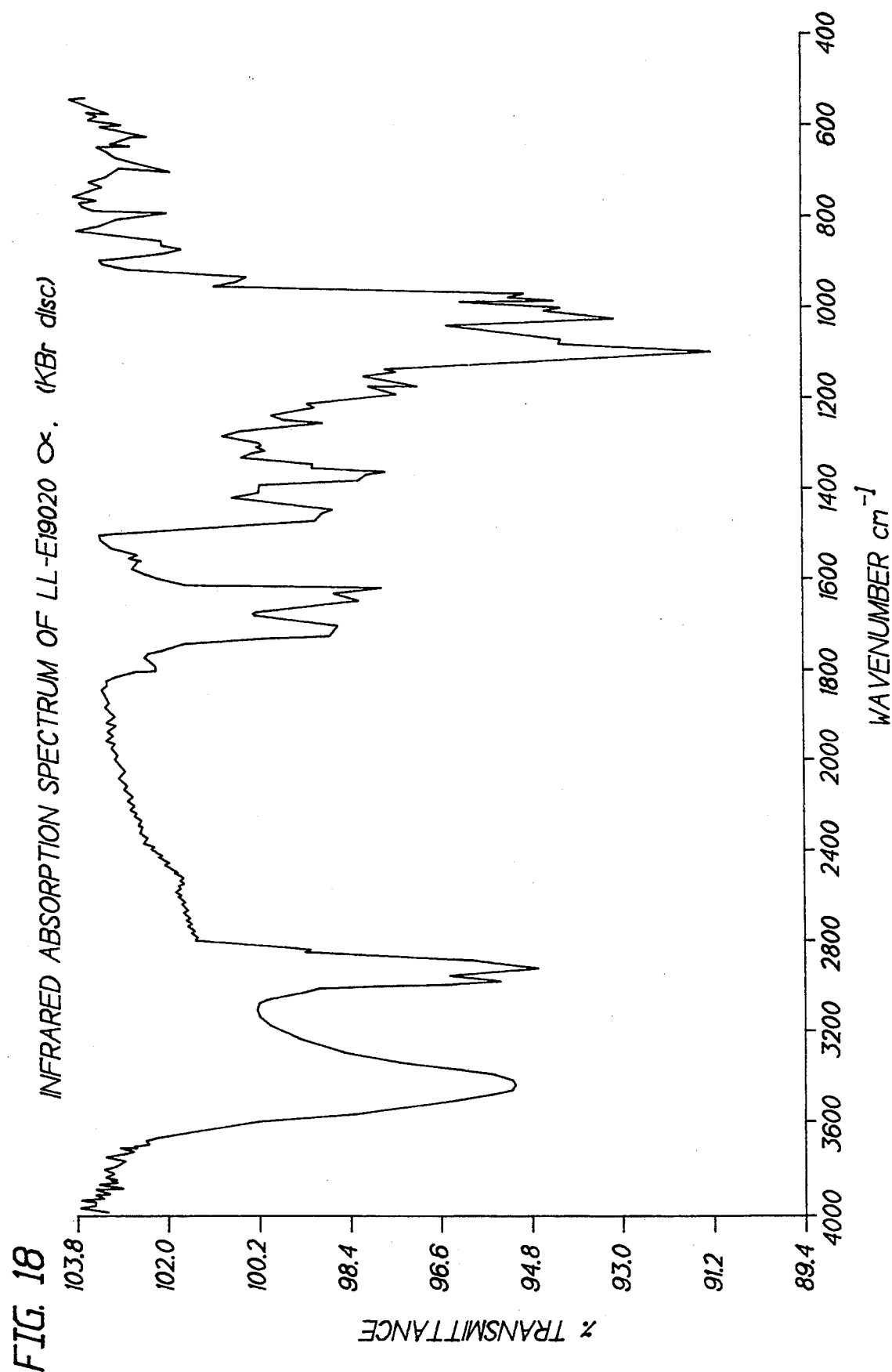
Figure 19:
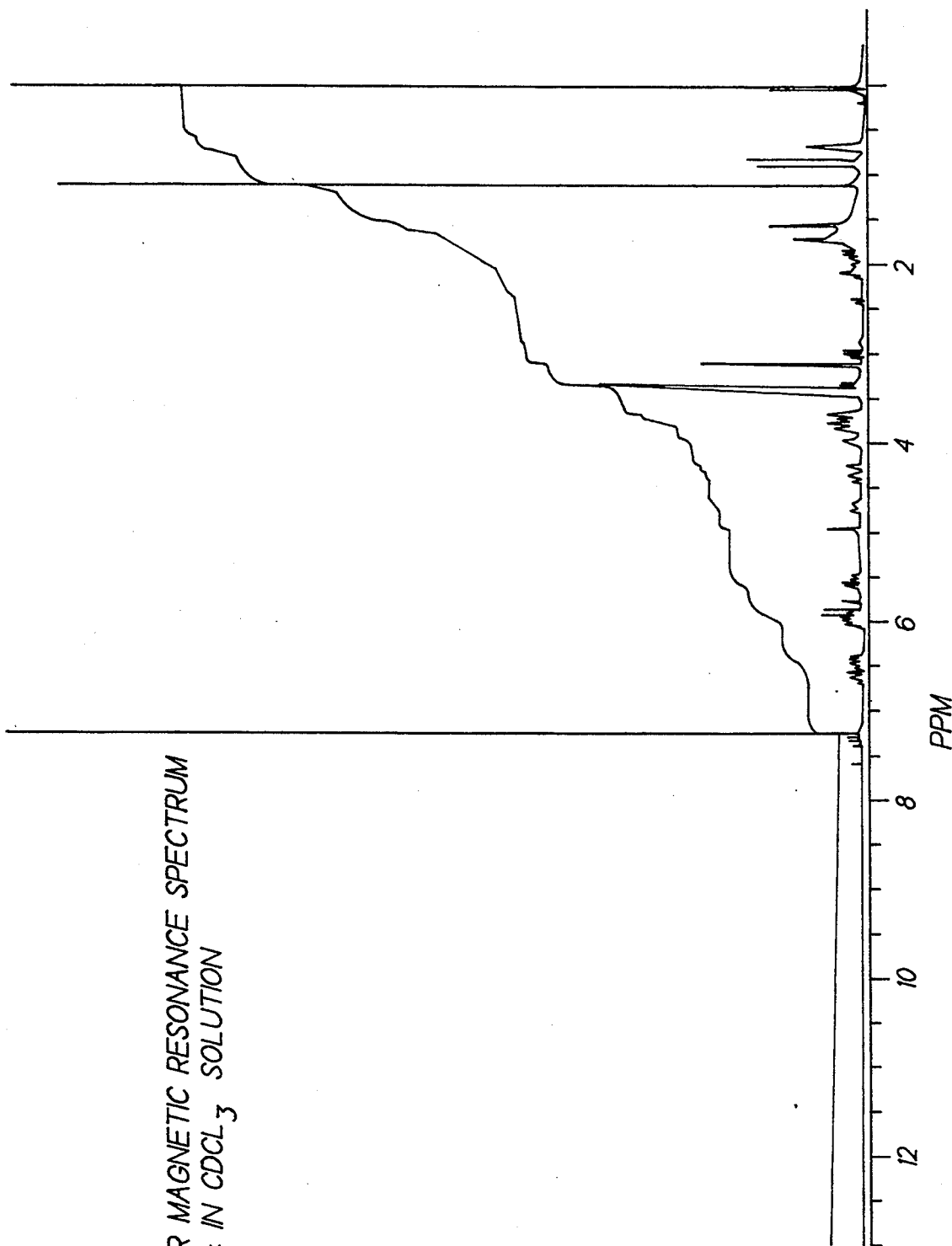
Figure 20:
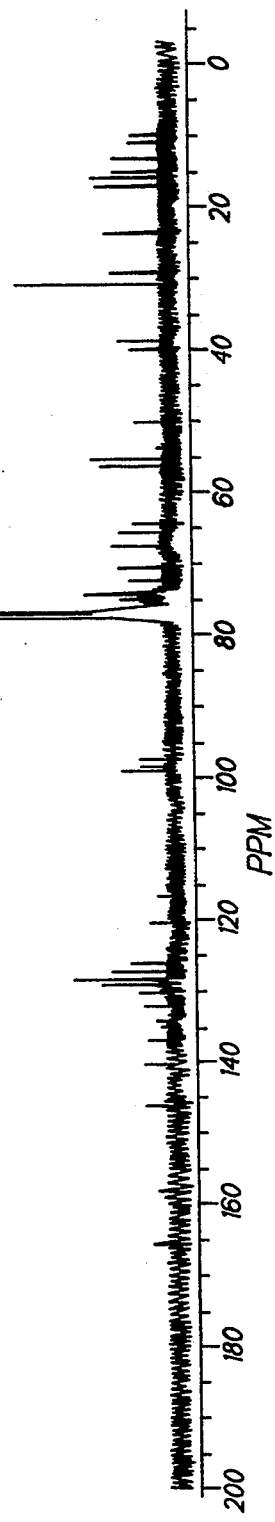
Figure 21:
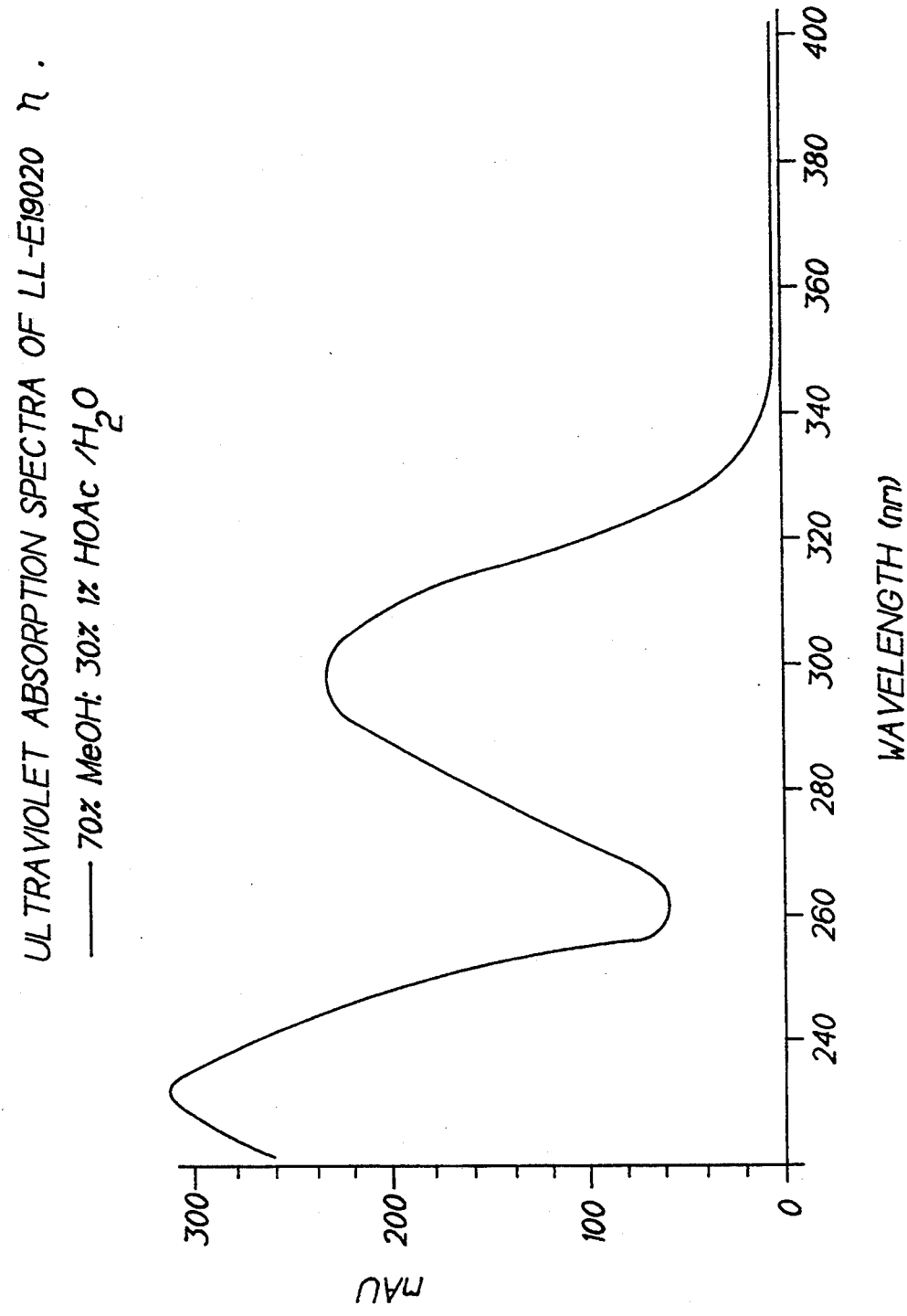

FIG. III shows the proton nuclear magnetic resonance spectrum of LL-E19020 Gamma.

FIG. IV shows the carbon-13 nuclear magnetic resonance spectrum of LL-E19020 Gamma.

FIG. V shows the ultraviolet absorption spectrum of LL-E19020 Alpha$_1$.

FIG. VI shows the infrared absorption spectrum of LL-E19020 Alpha$_1$.

FIG. VII shows the proton nuclear magnetic resonance spectrum of LL-E19020 Alpha$_1$.

FIG. VIII shows the carbon-13 nuclear magnetic resonance spectrum of LL-E19020 Alpha$_1$.

FIG. IX shows the ultraviolet absorption spectrum of LL-E19020 Epsilon.

FIG. X shows the infrared absorption spectrum of LL-E19020 Epsilon.

FIG. XI shows the proton nuclear magnetic resonance spectrum of LL-E19020 Epsilon.

FIG. XII shows the carbon-13 nuclear magnetic resonance spectrum of LL-E19020 Epsilon.

FIG. XIII shows the ultraviolet absorption spectrum of LL-E19020 Epsilon$_1$.

FIG. XIV shows the infrared absorption spectrum of LL-E19020 Epsilon$_1$.

FIG. XV shows the proton nuclear magnetic resonance spectrum of LL-E19020 Epsilon$_1$.

FIG. XVI shows the carbon-13 nuclear magnetic resonance spectrum of LL-E19020 Epsilon$_1$.

FIG. XVII shows the ultraviolet absorption spectrum of LL-E19020 Zeta.

FIG. XVIII shows the infrared absorption spectrum of LL-E19020 Zeta.

FIG. XIX shows the proton nuclear magnetic resonance spectrum of LL-E19020 Zeta.

FIG. XX shows the carbon-13 nuclear magnetic resonance spectrum of LL-E19020 Zeta.

FIG. XXI shows the ultraviolet absorption spectrum of LL-E19020 Eta.

FIG. XXII shows the infrared absorption spectrum of LL-E19020 Eta.

FIG. XXIII shows the proton nuclear magnetic resonance spectrum of LL-E19020 Eta.

FIG. XXIV shows the carbon-13 nuclear magnetic resonance spectrum of LL-E19020 Eta.

DETAILED DESCRIPTION OF THE INVENTION

In accordance with the invention, the antibiotic compound LL-E19020γ, LL-E19020ε, LL-E19020ε$_1$, LL-E19020α$_1$, LL-E19020ζ and LL-E19020η or a pharmacologically suitable salt thereof may be orally or parenterally administered to both monogastric and ruminant animals. The compound may be administered in admixture with the animal's feed or as a top dressing therefor. It may also be administered to the animal in the form of a bolus, pellet, tablet, pill, oral gel or the like or provided in the animal's drinking water.

When orally administered in or with the feed, generally a total concentration of 0,001 ppm to about 1,000 ppm of the antibiotic selected from LL-E19020$\gamma$, LL-E19020$\epsilon$, LL-E19020$\epsilon_1$, LL-E19020$\alpha_1$, LL-E19020$\zeta$ and LL-E19020$\eta$ or a pharmacologically acceptable salt thereof is effective for enhancing the growth rate and improving the efficiency of feed utilization by the host animal.

It is understood that since the antibiotics of the present invention are useful in the treatment of both monogastric and ruminant animals which may range in weight from only a few grams to as much as several thousand kilograms, the effective level of antibiotic required for treatment will vary. Further, effective levels for each animal will vary with the animal's stage of development and from species to species.

Compounds of this invention are particularly effective for inducing weight gain and improving feed efficiency in cattle, sheep, swine, goats, rabbits, horses and poultry.

Animal feed compositions which will provide the desired growth enhancement and feed efficiency in the meat-producing animal may be prepared by admixing the above-said antibiotic or salt thereof, or an animal feed supplement containing same, with a sufficient quantity of an appropriate animal feed to provide the desired level of active compound in the finished feed.

Animal feed supplements may be prepared by admixing about 1.0% to 75% by weight of the antibiotic or salt thereof, with about 99% to 25% by weight of carriers or diluents. Carriers or diluents suitable for use in the preparation of the feed supplements include the following: alfalfa meal, soybean meal, cottonseed oil meal, linseed oil meal, sodium chloride, corn meal, cane molasses, urea, bone meal, fish meal, corncob meal, calcium chloride, and other similar materials. Use of the carriers or diluents in feed supplements promote uniformity of distribution of the active ingredient in the finished feed into which the supplement is blended. It thus performs an important function by ensuring proper distribution of the active ingredient throughout the feed.

In actual agronomic practice, the supplement may be used as a top dressing to help ensure uniformity of distribution of the active compound across the top of the dressed feed.

For parenteral administration, the antibiotic or antibiotic salt may be prepared in the form of a paste or pellet and administered as an implant, usually under the skin of the head or ear of the animal in which enhanced growth rate and/or improved efficiency of feed utilization is desired.

In practice, parenteral administration generally involves injection of a sufficient amount of the above-said antibiotic, or antibiotic salt, to provide the animal with from about 0.01 to 100 mg/kg of body weight per day of the active ingredient.

Paste formulations may be prepared by dispersing the antibiotic or antibiotic salt in a pharmaceutically acceptable oil, such as, for example, peanut oil, sesame oil and corn oil.

Pellets containing an effective level of the antibiotic selected from LL-E19020$\gamma$, LL-E19020$\epsilon$, LL-E19020$\epsilon_1$, LL-E19020$\alpha_1$, LL-E19020$\zeta$ and LL-E19020$\eta$ may be prepared by admixing the antibiotic with a diluent, such as carbowax, biodegradable polaners, carnauba wax, or the like. A lubricant, such as magnesium stearate or calcium stearate, may be added to improve the pelleting process, if desired.

It is, of course, recognized that more than one pellet may be administered to an animal to achieve the desired dose level which will provide the increased growth rate and/or improve efficiency of feed utilization by said animal. Moreover, it has been found that additional implants may also be introduced periodically during the treatment period in order to maintain the proper drug release rate in the animal's body.

Advantageously, parenteral or oral administration of the antibiotic compounds of the present invention prevents, controls and ameliorates bacterial disease common to the current methods of livestock production. Among such diseases is swine dysentery, also known as bloody scours and hemorrhagic colitis, and which is frequently encountered in swine husbandry. This widespread disease is generally characterized by one or more of the following symptoms: diarrhea, hemorrhagic diarrhea, stunted growth, staggering gait, swelling of the eyelids and coarseness of the hair. Another important agronomic disease is necrotic enteritis, a severe intestinal disease encountered in poultry production. Both swine dysentery and necrotic enteritis, when left unchecked, have a significant economic impact on livestock production.

In accordance with this invention, for prophylactic administration, the antibiotic selected from LL-E19020$\gamma$, LL-E19020$\epsilon$, LL-E19020$\epsilon_1$, LL-E19020$\alpha_1$, LL-E19020$\zeta$ and LL-E19020$\eta$ or a pharmacologically suitable salt is intimately mixed in the feed ration or drinking water of the infected swine or poultry. The antibiotic may also be suitably prepared as a promix or 10 feed supplement as described hereinabove.

Further, parentoral administration of the antibiotics of this invention or the salts thereof to infected animals will yield the desired effect of controlling, ameliorating or diminishing the target disease. Parentoral administration may be achieved as described hereinabove.

The antibiotic compounds of the invention, LL-E19020$\gamma$, LL-E19020$\epsilon$, LL-E19020$\epsilon_1$, LL-E19020$\alpha_1$, LL-E19020$\zeta$ and LL-E19020$\eta$ are produced by fermentation of a strain of *Streptomyces lydicus*, SSP. tanzanius, NRRL 18036, in an aqueous nutrient medium containing assimilable sources of carbon and nitrogen under submerged aerobic conditions. This microorganism is maintained in the culture collection of the Medical Research Division, American Cyanamid Company, Pearl River, New York as culture number LL-E19020. A viable culture of this new microorganism has been deposited with the Patent Culture Collection Laboratory, Northern Regional Research Center, U.S. Department of Agriculture, Peoria, Illinois 61604, and has been added to its permanent collection. It has been assigned the strain designation NRRL 18036 by said depository.

Culture LL-E19020 produces short spiral spore chains, 10–50 spores long, with occasional longer chains. These tend to coalesce to form dry blackish masses on such ISP media as oatmeal and inorganic salts-starch. The spores have smooth surfaces as assessed by electron microscopy. The strain contains the L isomer of diaminopimelic acid, and may thus be assigned to the genus Streptomyces.

In the ISP tests for utilization of carbohydrates, LL-E19020 shows growth on arabinose, fructose, inositol, mannitol, reffinose, rhamnose, sucrose and xylose. Cellulose is not utilized.

In the Gordon Physiological Series, LL-E19020 differs from *Streptomyces lydicus* ISP 5461 in five (5) characteristics (xanthine hydrolysis, decarboxylation of oxalate, acid from erythritol, rhamnose and β-methyl-D-xyloside) and therefor, is designated as a subspecies of *Streptomyces lydicus*.

Cultivation of *Streptomyces lydicus* ssp. tanzanius NRRL 18036 may be carried out in a wide variety of liquid culture media. Media which are useful for the production of LL-E19020γ, LL-E19020ε, LL-E19020ε$_1$, LL-E19020α$_1$, LL-E19020ζ and LL-E19020η include an assimilable source of carbon, such as dextrin, sucrose, molasses, glycerol, etc; an assimilable source of nitrogen such as protein, protein hydrolysate, polypeptides, amino acids, corn steep liquor, etc; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicone oil may be added as needed.

The antibiotic LL-E19020 gamma is recovered from the fermentation broth by extraction of the broth into a solvent such as ethyl acetate, followed by chromatography of the ethyl acetate extracted broth using a high pressure liquid chromatography with a twelve (12) liter reverse phase column (C18 bonded phase 40 micron) using 0.1M ammonium acetate pH 4.3/acetonitrile (1:1) to obtain a partially mixture of LL-E19020 alpha and LL-E19020 gamma. Additional purification of this mixture is achieved by high pressure liquid chromatography.

The antibiotic LL-E19020 gamma is characterized by:

(a) the structure

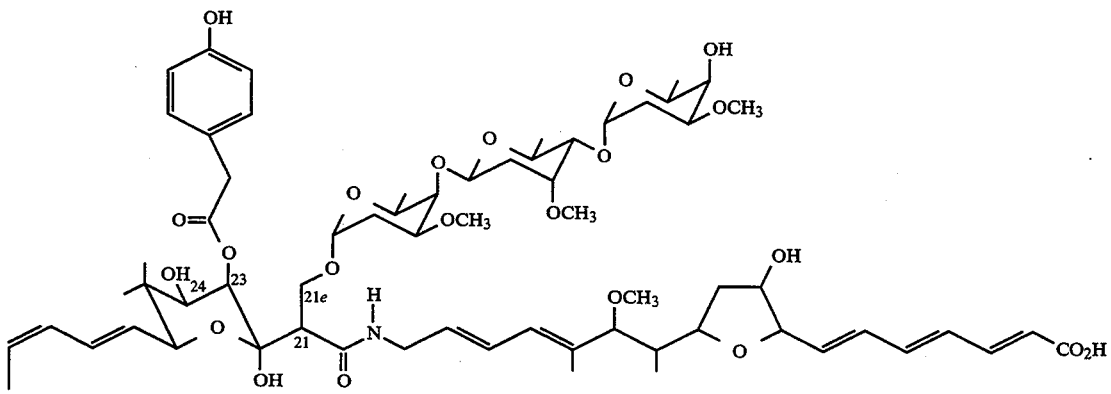

(b) an elemental analysis: C 62.22; H 7.77; N 0.92;
(c) a molecular weight of 1241 (FABMS=M/Z 1264 corresponding to [M+Na]+);
(d) a specific optical rotation: $[\alpha]_D^{26°} = -7°$ (1,001, MeOH)
(e) a characteristic ultraviolet absorption spectrum as shown in FIG. I of the attached drawings;
(f) a characteristic infrared absorption spectrum as shown in FIG. II of the attached drawings;
(g) a characteristic proton nuclear magnetic resonance spectrum as shown in FIG. III of the attached drawings;
(h) a characteristic carbon-13 nuclear magnetic resonance spectrum as shown in FIG. IV of the attached drawings;
(i) a characteristic HPLC retention time of 18.5 minutes using a gradient of acetonitrile in aqueous acetic acid; and
(j) a characteristic HPLC retention time of 19.6 minutes using a gradient of dioxane in aqueous acetic acid.

The antibiotics LL-E19020 epsilon and LL-E19020 epsilon$_1$ are recovered from the fermentation broth by extraction of the broth.

The antibiotic LL-E 19020 epsilon is characterized by:

(a) the structure

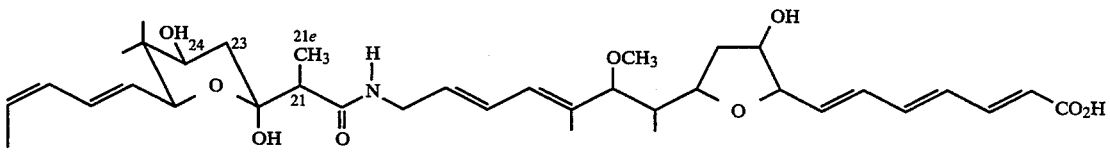

(b) a molecular weight of 643 (FABMS=M/Z 666 corresponding to [M+Na]+).
(c) a specific optical rotation: $[\alpha]_D^{26°} = +24°$(1.53, MeOH)
(d) a characteristic ultraviolet absorption spectrum as shown in FIG. IX of the attached drawings;
(e) a characteristic infrared absorption spectrum as shown in FIG. X of the attached drawings;
(f) a characteristic proton nuclear magnetic resonance spectrum as shown in FIG. XI of the attached drawings;

(g) a characteristic carbon-13 nuclear magnetic resonance spectrum as shown in FIG. XII of the attached drawings;

(h) a characteristic HPLC retention time of 12.6 minutes using a gradient of acetonitrile in aqueous acetic acid; and (i) a characteristic HPLC retention time of 11.4 minutes using a gradient of dioxane in aqueous acetic acid.

The antibiotic LL-E19020 alpha₁ is recovered from the fermentation broth by pH adjustment to 4.5-5.5, (g) a characteristic carbon-13 nuclear magnetic resonance spectrum as shown in FIG. VIII of the attached drawings; and (h) a characteristic HPLC retention time of 23.1 minutes using a gradient of dioxane in aqueous acetic acid.

The antibiotics LL-E19020 zeta and LL-E19020 eta are recovered from the fermentation broth by adsorption on a nonionic adsorption resin.

The antibiotic LL-E 19020 zeta is characterized by:
(a) the structure

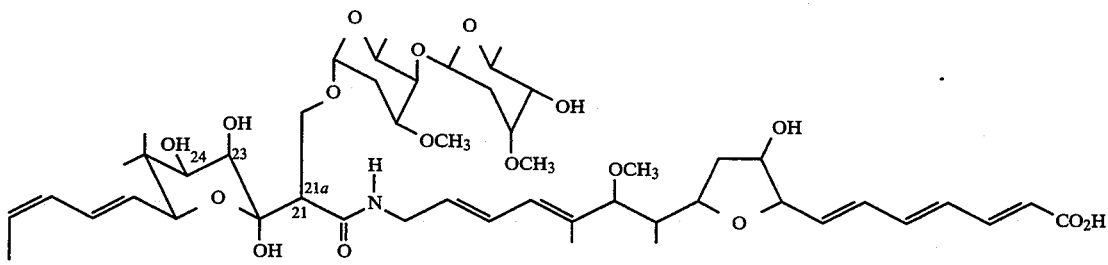

filtration through diatomaceous earth, extraction into a solvent such as ethyl acetate, concentration, dissolution in a solvent such as dichloromethane and purification by column chromatography on silica gel.

The antibiotic LL-E19020 alpha₁ is characterized by:
(a) the structure

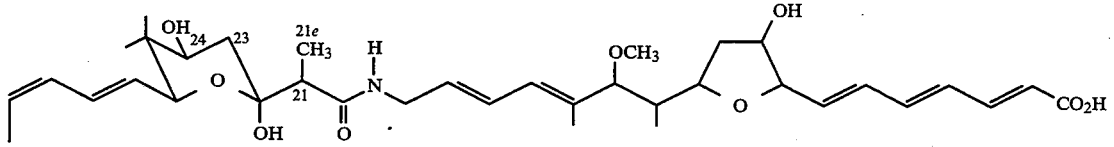

(b) a molecular weight of 1107 (FABMS=M/Z 1130 corresponding to [M+Na]+);

(c) a characteristic ultraviolet absorption spectrum as shown in FIG. XVII of the attached drawings;

(d) a characteristic infrared absorption spectrum as shown in FIG. XVIII of the attached drawings;

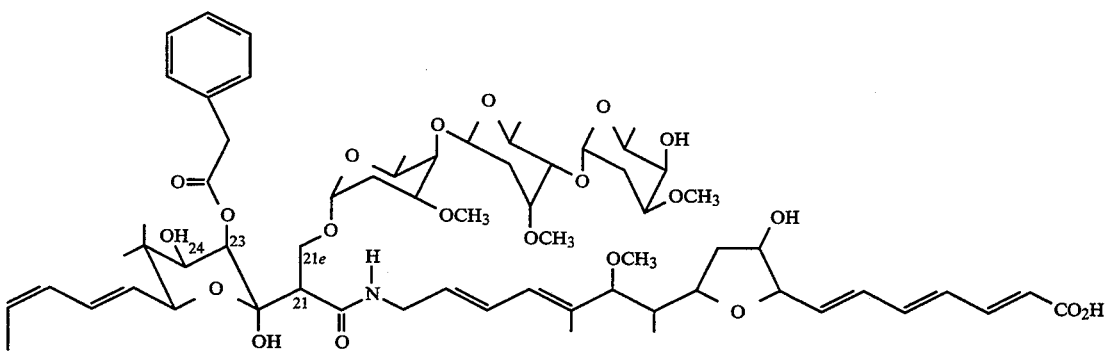

(b) a molecular weight of 1225 (FABMS=M/Z 1248 corresponding to [M+Na]+);

(c) a molecular formula: $C_{65}H_{95}NO_{21}$ (d) a characteristic ultraviolet absorption spectra as shown in FIG. V of the attached drawings;

(e) a characteristic infrared absorption spectrum as shown in FIG. VI of the attached drawings;

(f) a characteristic proton nuclear magnetic resonance spectrum as shown in FIG. VII of the attached drawings;.

(e) a characteristic proton nuclear magnetic resonance spectrum as shown in FIG. XIX of the attached drawings;

(f) a characteristic carbon-13 nuclear magnetic resonance spectrum as shown in FIG. XX of the attached drawings;

(g) a characteristic HPLC retention time of 13.2 minutes using a gradient of acetonitrile in aqueous acetic acid; and (h) a characteristic HPLC retention time 16.3 minutes using a gradient of dioxane in aqueous acetic acid.

The antibiotic LL-E 19020 eta is characterized by:
(a) the structure

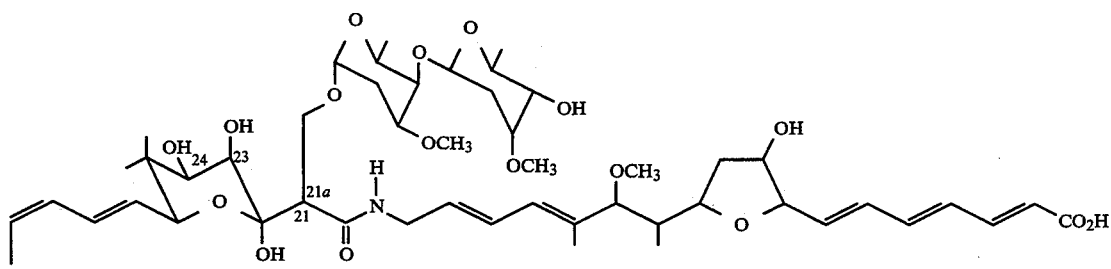

(b) a molecular weight of 963 (FABMS=M/Z 986 corresponding to [M+Na]+);
(c) a characteristic ultraviolet absorption spectrum as shown in FIG. XXI of the attached drawings;
(d) a characteristic infrared absorption spectrum as shown in FIG. XXII of the attached drawings;
(e) a characteristic proton nuclear magnetic resonance spectrum as shown in FIG. XXIII of the attached drawings;
(f) a characteristic carbon-13 nuclear magnetic resonance spectrum as shown in FIG. XXIV of the attached drawings;
(g) a characteristic HPLC retention time of 11.5 minutes using a gradient of acetronitrile in aqueous acetic acid; and
(h) a characteristic HPLC retention time of 14.2 minutes using a gradient of dioxane in aqueous acetic acid.

For a clearer understanding of the invention, specific examples of it are set forth below. These examples are merely illustrative, and are not to be understood as limiting the scope and underlying principles of the invention in any way.

EXAMPLE 1

Evaluation of test compound for increasing the growth of chickens and improving the efficiency of feed utilization thereby In this test, one day old Peterson X Arbor Acres chicks are sorted into equal weight groups of 5 males and 5 females per cage. Cages are randomized to treatment groups with six replicates per treatment. The test compound is evaluated 25 ppm in the diet against chicks receiving a non-medicated diet and a diet containing 200 ppm of penicillin as a positive control.

The cages are weighed at day 1 and at day 14 and feed consumption is measured on weigh days. Feed and water are offered ad libitum and lighting and supplemental heat are provided continuously.

The poultry diet employed in the test is as follows:

| | |
|---|---|
| Vitamin-amino acid premix | 0.5% |
| Trace minerals | 0.1% |
| Sodium chloride | 0.3% |
| Dicalcium phosphate | 1.2% |
| Ground limestone | 0.5% |
| Stabilized fat | 4.0% |
| Dehydrated alfalfa, 17% protein | 2.0% |
| Corn gluten meal, 41% protein | 5.0% |
| Menhaden fish meal, 60% protein | 5.0% |
| Soybean oil meal, 44% protein | 30.0% |
| Ground yellow corn | 100.0% |

The vitamin-amino acid premix in the above feed composition is prepared from the following formulation. The expressions of quantity relate to units per kilogram of the finished feed composition.

| | |
|---|---|
| Butylated hydroxy toluene | 125.0 mg |
| dl-Methionine | 500.0 mg |
| Vitamin A | 3300.0 I.U. |
| Vitamin $D_3$ | 1100.0 I.C.U. |
| Riboflavid | 4.4 mg |
| Vitamin E | 2.2 I.U. |
| Niacin | 27.5 mg |
| Panthothenic acid | 8.8 mg |
| Choline chloride | 500.0 mg |
| Folic acid | 1.43 mg |
| Menadione sodium bisulfate | 1.1 mg |
| Vitamin $B_2$ | 11.0 mcg |
| Ground yellow corn | 5.0 mg |

Data obtained are reported in Table I below where it can be seen that antibiotic LL-E19020γ both improved weight gain of chicks and increased the efficiency of feed utilization thereby over unmedicated controls.

TABLE I

| Treatment | ppm | Weight Gain (g) | % improvement over control | feed conversion | % improvement over control |
|---|---|---|---|---|---|
| Control | — | 321 | — | 1.322 | — |
| E19020 gamma | 25 | 342 | 6.5 | 1.297 | 1.9 |
| Penicillin | 200 | 344 | 7.2 | 1.317 | 0.4 |

EXAMPLE 2

Inoculum Preparation

A typical medium used to grow the primary inoculum is prepared according to the following formula:

| | wt./vol. |
|---|---|
| Dextrose | 1.0% |
| Dextrin | 2.0% |
| Yeast extract | 0.5% |
| NZ Amine A | 0.5% |
| Calcium carbonate | 0.1% |
| Antifoam | 0.3% |
| Water qs | 100.0% |

NOTE: NZ Amine A is a pancreatic digest of casein, registered trademark of Scheffield Chemical, Norwich, New York. The term "qs" designates quantity sufficient i.e., a sufficient quantity of water to achieve a total volume of 100%.

This medium is sterilized and 100 ml, in a 500 ml flask, is inoculated with Streptomyces lydicus ssp. tanzanius NRRL 18036. The medium is then placed on a rotary shaker and incubated at 28° C. for 48 hours providing a primary inoculum. This primary inoculum is the used to inoculate 10 liters of the same sterile medium in a bottle.

This culture is grown for 24 hours providing secondary inoculum. This secondary inoculum is then used to inoculate 300 liters of the same sterile medium in a tank. This culture is grown at 30° C. for 44 hours with a sterile air flow of 0.66 liters per liter of mash per minute and agitation by an impeller driven at 200 rpm, providing a tertiary inoculum.

EXAMPLE 3

Fermentation I

A fermentation production medium of the following formulation is prepared:

|  | wt./vol. |
| --- | --- |
| Dextrin | 7.0% |
| Dextrose | 0.5% |
| soy flour | 1.5% |
| Corn Steep liquor | 0.5% |
| Calcium carbonate | 0.5% |
| Silicone antifoam | 0.3% |
| Water qs | 100.0% |

This medium is sterilized and 1500 liters is then inoculated with 150 liters of tertiary inoculum from Example 1. The fermentation is conducted at 28° C. with a sterile air flow of 3.3 liters of air per liter of mash per minute and agitation by an impeller driven at 100 rpm for 123 hours, at which time the mash is harvested.

EXAMPLE 4

Fermentation II

A fermentation medium of the following formulation is prepared:

|  | wt./vol. |
| --- | --- |
| Dextrin | 7.0% |
| Dextrose | 0.5% |
| Soy flour | 1.5% |
| corn steep Liquor | 0.5% |
| Calcium carbonate | 0.5% |
| Silicone antifoam | 0.3% |
| Water qs | 100.0% |

This medium is sterilized and 3000 liters is then inoculated with 300 liters of tertiary inoculum similarly prepared as in Example 1. The fermentation is conducted at 28° C. with a sterile air flow of 6.5 liters of air per liter of mash per minute and agitation by an impeller driven at 100 rpm for 89 hours, at which time the mash is harvested.

EXAMPLE 5

Fermentation III

A fermentation medium of the following formulation is prepared:

|  | wt./vol. |
| --- | --- |
| Dextrin | 7.0% |
| Dextrose | 0.5% |
| Soy flour | 1.5% |
| Corn steep liquor | 0.5% |
| Calcium carbonate | 0.5% |
| Silicone antifoam | 0.3% |
| Water qs | 100.0% |

This medium is sterilized and is then inoculated with 10 liters of secondary inoculum from Example 1 to a final volume of 300 liters. The fermentation is conducted at 30° C. with a sterile air flow of 0.67 liters of air per liter of mash per minute and agitation by an impeller driven at 200 rpm for 92–93 hours, at which time the mash is harvested.

EXAMPLE 6

Fermentation IV

A fermentation medium of the following formulation is prepared.

|  | wt./vol. |
| --- | --- |
| Dextrin | 3.0% |
| Molasses | 2.0% |
| Soy peptone | 0.75% |
| Yeast extract | 0.25% |
| Calcium carbonate | 0.2% |
| Water qs | 100.0% |

This medium is sterilized and 2700 liters is then inoculated with 300 liters of tertiary inoculum from Example 1. The fermentation is conducted at 28° C. with a sterile air flow of 0.55 liters of air per liter of mash per minute and agitation by an impeller driven at 100 rpm for 113 hours, at which time the mash is harvested.

EXAMPLE 7

Isolation and Purification of LL-E19020 Gamma

The harvest mash from two (2) fermentations conducted as described in Example 3 and Example 4, making a total volume of 3200 liters, is diluted with 1600 liters of methyl alcohol and filtered through diatomaceous earth. The filter cake is washed with 320 liters of water and the wash is added to the filtrate giving a total volume of 5000 liters. A 800 liter volume is charged to a still and evaporated to 500 liters. This procedure is repeated until the total volume is reduced to 2950 liters followed by dilution with 1450 liters of ethyl acetate. The lower phase is removed and the upper phase of 900 liters evaporated to 79.5 liters. This concentrate is diluted with 80 liters of ethyl acetate and the lower layer removed. The upper layer is evaporated to give 2.4 liters of a syrup. This crude product is repeatedly decanted with hexane then dissolved in methyl alcohol and applied portion wise to a 12 liter reverse phase column (C18 bonded phase 40 micron). In a typical run, 400 ml of syrup is dissolved in methyl alcohol to give a final volume of 700 ml which is applied to the reverse phase column and eluted with 1:10.1M ammonium acetate:acetonitrile at pH 4.3 to afford, upon evaporation of the volatiles, 38 g of impure LL-E19020 Gamma. Several like runs are completed in this manner and the products combined.

Purification of LL-E19020 Alpha and LL-E19020 Gamma

A total of 100 g of impure LL-E19020 Gamma is charged to a 12 liter reverse phase column (C18 bonded phase 40 micron) and eluted with 0.1M ammonium acetate buffer pH 4.3/acetonitrile (1:1). Fractions designated F1–F28, each having a volume of 20 liters are collected. Fraction F4 is stirred with 15 liters of methylene chloride for 1 hour. The methylene chloride layer is separated and evaporated to 1 liter, dried with calcium chloride and evaporated to a residue which is dissolved in 75 ml of methyl alcohol and filtered. The filtrate is added, 5 ml at a time, to a 2.2×25 cm (10 micron) reverse phase C18 chromatographic column. The column is eluted with 40% acetonitrile in 0 05M ammonium acetate buffer (pH 4.5) at a flow rate of 9.9 ml/minute. The eluate collected after 2.5 to 3 hours is extracted with ethyl acetate. The organic layer is evaporated to a syrup which is dissolved in t-butanol and freeze-dried to afford 160 mg of pure LL-E19020 Gamma

ANALYTICAL HIGH PRESSURE LIQUID CHROMATOGRAPHY (HPLC)

The LL-E19020 Gamma component is analyzed using two different analytical HPLC systems. Retention time compared to E19020 and are given in the table below.

| COMPONENTS | RETENTION TIME (MINUTES) | |
|---|---|---|
| | SYSTEM A | SYSTEM B |
| LL-E19020α | 22.7 | 23.5 |
| LL-E19020β | 27.6 | 26.7 |
| LL-E19020γ | 18.5 | 19.6 |

A. HPLC system: Alltech adsorbosphere HS 5μ C18 column (4.6×250 mm) with guard column, eluted with a gradient of acetonitrile in 1% aqueous acetic acid. The starting composition is 40% acetonitrile linearly increasing to 70% over 25 minutes and holding at for 5 minutes. The flow rate is 1.0 mL per minute.

B. HPLC system: Alltech adsorbosphere HS 5μ C18 (4.6×250 mm) with guard column, eluted with a gradient of dioxane in 1% aqueous acetic acid. The starting composition is 55% dioxane, increasing to over 25 minutes and holding at 70% for 5 minutes. The flow rate is 1.0 mL per minutes.

EXAMPLE 8

Isolation and Purification of LL-E19020 Epsilon and LL-E19020 Epsilon₁

The harvest mash from two (2) fermentations conducted as described in Example 5 making a total volume of 503 liters is diluted with 6 liters of toluene. The pH is adjusted to 4.5 using concentrated hydrochloric acid. While stirring, 250 liters of methyl alcohol is added. Stirring is continued over 2 hours and the pH is continuously monitored. To the mixture is added 50 pounds of diatomaceous earth followed by stirring for 15 minutes. The mixture is filtered through a filter press with the press washed with 75 liters of water. The total volume collected is 697 liters. A 45 liter HP-20 column is prepared by washing the resin with 100 liters of deionized water at a rate of 1 to 2 liters/minute followed by 120 liters of 1:1 1N sodium hydroxide/methyl alcohol at a rate of 1 to 2 liters/minute followed by 100 liters of deionized water at a rate of 1 to 2 liters/minute followed by 120 liters of 1N sulfuric acid at a rate of 1 to 2 liters/minute followed by 100 liters of deionized water at a rate of 1 to 2 liters/minute. The pH of the eluate is checked and additional deionized water wash could be needed to bring the pH to between 6 and 7. The column is further washed with 100 liters of methyl alcohol at a rate of 1 to 2 liters/minute followed by 100 liters of deionized water. The column is further washed at a rate of I to 2 liters/minute with a solution of 108 liters of acetone and 12 liters of water followed by 100 liters of acetone at a rate of 1 to 2 liters/minute and concluded with 100 liters of deionized water at a rate of 1 to 2 liters/minute. The 697 liters of liquid from the filter press is added to the prepared HP-20 column at a rate of 1 liter/minute. The column is further washed with 120 liters of deionized water at a rate of 1 liter/minute followed by a solution of 64 liters of deionized water and 16 liters of acetone at a rate of 1 liter/minute. Four 20 liter fractions are collected and designated F1–F4. The column is further washed with a solution made from 48 liters of deionized water and 32 liters of acetone at a rate of 0.5 to 1 liter/minute to afford four 20 liter fractions which are collected and labeled F1–F8. Further washing of the column with a solution made from 32 liters of deionized water and 48 liters of acetone at a rate of 0.5 to 1 liter/minute affords four 20 liter collected fractions designated F9–F12. The column is further washed with a solution made from 16 liters of water and 64 liters of acetone at a rate of 0.5 to 1 liter/minute to afford four 20 liter collected fractions designated as F13–F16. Further washing of the column with acetone at a rate of 0.5 to 1 liter/minute affords four 20 liter collected fractions designated F17–F20. Fraction 16 is concentrated and freeze-dried to afford 36.8 g of material which is purified by high pressure liquid chromatography (HPLC) on a $C_{18}$ reverse phase column (5.0×25 cm) by elution with 50-52% dioxane in 1% aqueous acetic acid. Thirteen fractions are collected. Fraction 5 is evaporated to afford 121 mg of LL-E19020 Epsilon. Fraction 2 is further purified by high pressure liquid chromatography on a $C_{18}$ reverse phase column (5.0×25 cm) by elution with 30% acetonitrile in 1% acetic acid to afford 19.5mg of LL-E19020 Epsilon₁.

ANALYTICAL HIGH PRESSURE LIQUID CHROMATOGRAPHY (HPLC)

The LL-E19020 Epsilon and Epsilon₁ components are analyzed using two different analytical HPLC systems. Their retention time compared to LL-E19020 α and β are indicated in the table below.

| COMPONENTS | RETENTION TIME (MINUTES) | |
|---|---|---|
| | SYSTEM A | SYSTEM B |
| LL-E19020 Alpha | 22.7 | 23.5 |
| LL-E19020 Beta | 27.6 | 26.7 |
| LL-E19020 Epsilon | 12.6 | 11.4 |
| LL-E19020 Epsilon₁ | 9.9 | 9.4 |

A. HPLC system: Alltech adsorbosphere HS 5C18 column (4.6×250 mm) with guard column, eluted with a gradient of acetonitrile in 1% aqueous acetic acid. The starting composition is 40% acetonitrile linearly increasing to 70% over 25 minutes and holding at 70% for 5 minutes. The flow rate is 1.0 mL per minute.

B. HPLC system: Alltech adsorbosphere HS 5μ C18 (4.6×250 mm) with guard column, eluted with a gradient of dioxane in 1% aqueous acetic acid. The starting composition is 55% dioxane, increasing to 70% over 25 minutes and holding at 70for 5 minutes The flow rate is 1.0 mL per minutes.

EXAMPLE 9

Isolation and Purification of LL-E19020 Alpha₁

The harvest mash from two fermentations conducted as described in Example 6 are combined, making a total of 6000 liters, adjusted to pH 5 with hydrochloric acid and filtered through diatomaceous earth. The filtrate is extracted with ethyl acetate and the extract concentrated to a syrup.

This crude syrup is dissolved in methanol and applied to a 12 liter reverse-phase column (C18 bonded phase 40 micron). The column is eluted with acetonitrile, 0.1M ammonium acetate buffer pH 4.3 (1:1) at a rate of 1.0 liter per minute. Thirteen 24 liter fractions are collected. Fraction 7 contains impure LL-E19020$\alpha_1$. The antibiotic is extracted from the mobile phase using dichloromethane followed by evaporation and freeze drying from t-butanol, giving a white solid.

The product of several fermentations as described above are combined to give 1700 g of solid.

Samples of this solid are purified using the following chromatographic techniques.

A 0.5 g sample is dissolved in a mixture of 4:1 dioxane/1% HOAc and injected onto a 2.5×50 cm $C_8$ reverse phase column. The column is eluted with 52.5% dioxane/47.5%:1% HOAc in water at a flow rate of 10 ml/min. After a forerun of 1100 ml, which is discarded, fractions are collected at 2.5 min intervals. Fractions are analyzed by analytical HPLC and combined. Fractions 40–48 contain E19020$\alpha_1$.

A 0.5 g sample is dissolved in a 1:1 mixture of 4:1 dioxane/1% HOAc and 100% dioxane and injected onto a 2.5×50 cm $C_8$ reverse phase column. The column is eluted with a mixture of dioxane:water:acetic acid (3150:2850:60) at a flow rate of 9.9 ml/min. After a brief forerun, fractions are collected at 2.5 min intervals. Fractions are analyzed by analytical HPLC and combined. Fractions 23–29 contain E19020$\alpha_1$.

A 0.877 g sample is dissolved in a 1:1 mixture of 4:1 dioxane/1% HOAc and 100% dioxane and injected onto a 2.5×50 cm $C_8$ reverse phase column. The column is eluted with a mixture of dioxane:water:acetic acid (3150:2850:60) at a flow rate of 9.9 ml/min. After a 200 min forerun, fractions are collected from 200–230 min and contain E19020$\alpha_1$.

A 1.0 g sample is dissolved in a 1:1 mixture of 4:1 dioxane/1% HOAc and 100% dioxane and injected onto a $C_{18}$ column (5.0×60 cm). The column is eluted with a mixture of dioxane:water:acetic acid (3150:2850:60) at a flow rate of 25 ml/min. After a forerun of S liters fractions are collected at 1 min intervals. Fractions are analyzed by analytical HPLC and combined accordingly: fractions 30–84 contain E19020$\alpha_1$. The combined fractions from the above chromatographic separations are pooled and evaporated to give 200 mg which is subjected to chromatography on a $C_8$ column (2.5×50 cm) by elution with 1:1 dioxane/1% acetic acid.

The above 200 mg is dissolved in 1:1 dioxane:water and charged to the chromatography column and eluted with 1:1 dioxane/1% acetic acid at a rate of 10 ml/min. After 10.5 hours the product began to elute. Fractions are analyzed by HPLC. Fractions 40–80 are combined to afford after evaporation 18 mg of LL-E19020$\alpha_1$.

ANALYTICAL HIGH PRESSURE LIQUID CHROMATOGRAPHY (HPLC)

The LL-E19020 Alpha$_1$ component is analyzed by analytical HPLC. Its retention time compared to LL-E19020 $\alpha$ and $\beta$ is given in the Table below.

| COMPONENTS | RETENTION TIME (MINUTES) SYSTEM B |
|---|---|
| LL-E19020$\alpha$ (alpha) | 23.5 |
| LL-E19020$\beta$ (beta) | 26.7 |
| LL-E19020$\alpha_1$ (alpha$_1$) | 23.1 |

B. HPLC system: Alltech adsorbosphere HS 5$\mu$ C18 (4.6×250 mm) with guard column, eluted with a gradient of dioxane in 1% aqueous acetic acid. The starting composition is 55% dioxane, increasing to 70% over 25 minutes and holding at 70% for 5 minutes. The flow rate is 1.0 mL per minute.

EXAMPLE 10

Isolation and Purification of LL-E19020 Zeta and LL-E19020 Eta

The harvest mash from two (2) fermentations conducted as described in Example 5 making a total volume of 503 liters is diluted with 6 liters of toluene. The pH is adjusted to 4.5 using concentrated hydrochloric acid. While stirring, 250 liters of methyl alcohol is added. Stirring is continued over 2 hours and the pH is continuously monitored. To the mixture is added 50 pounds of diatomaceous earth followed by stirring for 15 minutes. The mixture is filtered through a filter press with the press washed with 75 liters of methyl alcohol. The total volume collected is 697 liters. A 45 liter HP-20 column is prepared by washing the resin with 100 liters of deionized water at a rate of 1 to 2 liters/minute followed by 120 liters of 1:1 1N sodium hydroxide/methyl alcohol at a rate of 1 to 2 liters/minute followed by 120 liters of 1N sulfuric acid at a rate of 1 to 2 liters/minute followed by 100 liters of deionized water at a rate of 1 to 2 liters/minute. The pH of the eluate is checked and additional deionized water wash could be needed to bring the pH to between 6 and 7. The column is further washed with 100 liters of methyl alcohol at a rate of 1 to 2 liters/minute followed by 100 liters of deionized water. The column is further washed at a rate of 1 to 2 liters/minute with a solution of 108 liters of acetone and 12 liters of water followed by 100 liters of acetone at a rate of 1 to 2 liters/minute and concluded with 100 liters of deionized water at a rate of 1 to 2 liters/minute. The 697 liters of liquid from the filter press is added to the prepared HP-20 column at a rate of 1 liter/minute. The column is further washed with 120 liters of deionized water at a rate of 1 liter/minute followed by a solution of 64 liters of deionized water and 16 liters of acetone at a rate of I liter/minute. Four 20 liter fractions are collected and designated F1–F4. The column is further washed with a solution made from 48 liters of deionized water and 32 liters of acetone at a rate of 0.5 to 1 liter/minute to give four 20 liter fractions which are collected and labeled F5–F8. Further washing of the column with a solution made from 32 liters of deionized water and 48 liters of acetone at a rate of 0.5 to 1 liter/minute affords four 20 liter collected factions designated F9–F12. The column is further washed with a solution made from 16 liters of water and 64 liters of acetone at a rate of 0.5 to 1 liter/minute to afford four 20 liter collected fractions designated as F13–F16. Further washing of the column with acetone at a rate of 0.5 to 1 liter/minute affords four 20 liter fractions designated F17–F20. Fraction 16 is concentrated and freeze dried to afford 36.8 g of material which is purified by high pressure liquid chromatography (HPLC) on a C18 reverse phase column (5.0×25 cm) by elution with 50-52% dioxane in 1% aqueous acetic acid. Thirteen fractions are collected from the HPLC. Fraction 9 is further purified by high pressure liquid chromatography on a $C_{18}$ reverse phase column (2.5×25 cm) by elution with 65% methyl alcohol in 1% acetic acid to afford 16.0mg of LL-E19020 Eta. Fraction 13 is further purified by reverse phase chromatography on a $C_{18}$ column (2.5×25 cm) by elution with 67.5% methyl alcohol in 1% acetic acid to afford 29.3 mg of LL-E19020 Zeta.

ANALYTICAL HIGH PRESSURE LIQUID CHROMATOGRAPHY (HPLC)

The LL-E19020 Eta and Zeta components are analyzed using two different analytical HPLC systems Their retention times compared to LL-E19020 $\alpha$ and $\beta$ are indicated below:

| COMPONENTS | RETENTION TIME (MINUTES) | |
|---|---|---|
| | SYSTEM A | SYSTEM B |
| LL-E19020$\alpha$ (alpha) | 22.7 | 23.5 |
| LL-E19020$\beta$ (beta) | 27.6 | 26.7 |
| LL-E19020$\eta$ (eta) | 11.5 | 14.2 |
| LL-E19020$\zeta$ (zeta) | 13.2 | 16.3 |

A. HPLC system: Alltech adsorbosphere HS 5$\mu$ C18 column (4.6×250 mm) with guard column, eluted with a gradient of acetonitrile in 1% aqueous acetic acid. The starting composition is 40% acetonitrile linearly increasing to 70% over 25 minutes and holding at 70% for 5 minutes. The flow rate is 1.0 mL per minute.

B. HPLC system: Alltech adsorbosphere HS 5$\mu$ C18 (4.6×250 mm) with guard column, eluted with a gradient of dioxane in 1% aqueous acetic acid. The starting composition is 55% dioxane, increasing to 70% over 25 minutes and holding at 70% for 5 minutes. The flow rate is 1.0 mL per minutes.

EXAMPLE 11

In Vitro Antibacterial Activity Of LL-E19020 Gamma

The in vitro antibacterial activity of LL-E19020 Gamma is determined against a spectrum of gram positive and gram negative bacteria by a standard agar dilution method. Mueller-Hinton agar containing 5% sheep blood and two-fold decreasing concentrations after 18 hours incubation is recorded as the minimal inhibitory concentration for that strain.

Minimum Inhibitory Concentration Procedure By Agar Dilution

1. Serial two-fold dilutions of drug are prepared in Mueller-Hinton broth in a range of 2560 g/ml–0.15 g/ml plus a solvent control.
2. Two milliliters of drug dilution (10×) are added to sterile screw cap bottles to which 18 ml of Mueller-Hinton agar containing 5.6% defibrinated sheep blood is added. Final drug concentration ranges 256 g/ml–0.015 g/ml in agar containing 5% sheep blood.
3. A few isolated colonies of each test organism are inoculated into 5 ml trypticase soy broth or brain heart infusion broth. The cultures are shaken at 35° C. for 5 hours.
4. Each culture is diluted 1:50 ($10^{-1.7}$) in Mueller-Hinton broth and applied to agar plates using a Steers replicator. Control plates should be seeded last to ensure that viable organisms are present throughout the procedure. Inoculated agar plates are allowed to stand undisturbed until the inoculum spots are completely absorbed.
5. The plates are inverted and incubated at 35° C. for 18 hours with $CO_2$,
6. The minimum inhibitory concentration (MIC) is taken as the lowest concentration of anti microbial agent at which complete inhibition of antimicrobial agent at which complete inhibition occurs. A very fine, barely visible haze or a single colony is disregarded.

| In Vitro Activity of LL-E19020 Gamma MINIMAL INHIBITORY CONCENTRATION (MCG/ML) | |
|---|---|
| ORGANISM | LL-E19020 GAMMA |
| 1. *Staphylococcus aureus* NEMC 87-69 | 32 |
| 2. *Staphylococcus aureus* ROSE (MP)* | 32 |
| 3. *Staphylococcus aureus* IVES 160 | 32 |
| 4. *Staphylococcus aureus* IVES 396 | 64 |
| 5. *Staphylococcus aureus* VGH 84-47 | 64 |
| 6. *Staphylococcus aureus* CMC 83-131 | 64 |
| 7. *Staphylococcus aureus* SMITH (MP) | 128 |
| 8. *Staphylococcus aureus* ATCC 25923 | >128 |
| 9. *Staphylococcus aureus* ATCC 29213 | 128 |
| 10. *Staphylococcus haemolyticus* AVAH 88-1 | 64 |
| 11. *Staphylococcus haemolyticus* AVAH 88-3 | 16 |
| 12. *Staphylococcus epidermidis* IVES 455 | 16 |
| 13. *Enterococcus spp.* ARUM 87-41 | 8 |
| 14. *Enterococcus spp.* CHBM 88-60 | 16 |
| 15. *Enterococcus spp.* WRVA 88-33 | 16 |
| 16. *Enterococcus spp.* UCI 85-30 | 16 |
| 17. *Enterococcus spp.* VGH 84-69 | 16 |
| 18. *Enterococcus spp.* CMC 83-120 | 16 |
| 19. *Streptococcus pyogenes* AMCH 88-84 | 0.12 |
| 20. *Streptococcus pyogenes* AMCH 88-86 | 0.5 |
| 21. *Streptococcus pyogenes* C203 (MP) | 0.12 |
| 22. *Streptococcus pneumoniae* SV-1 (MP) | 0.12 |
| 23. *Streptococcus pneumoniae* CHBM 88-75 | 16 |
| 24. *Streptococcus pneumoniae* TEX 85-2 | 0.5 |
| 25. *Bacillus cereus* DAVIES | 32 |
| 26. *Klebsiella pneumoniae* NEMC 87-271 | >128 |
| 27. *Escherichia coli* ATCC 25922 | >128 |
| 28. *Escherichia coli* ATCC 35218 | >128 |
| 29. *Pseudomonas aeruginosa* 12-4-4 (MP) | >128 |

*MP = Mouse passage used in in vivo studies

As can be seen from the in vitro data above, LL-E19020 Gamma demonstrated relatively good activity against non-enterococcal streptococci (MIC 0.12–16 $\mu$g/ml).

EXAMPLE 12

In Vitro Antibacterial Activity of LL-E19020 Epsilon and LL-E19020 Epsilon$_1$ is determined against a spectrum of gram positive and gram negative bacteria according to the procedure described in Example 11.

IN VITRO ACTIVITY OF LL-E19020 EPSILON
AND LL-E19020 EPSILON
MINIMAL INHIBITORY CONCENTRATION (MCG/ML)

| ORGANISM | LL-E19020 EPSILON EPSILON | ELSIPON | EPSILON$_1$ |
|---|---|---|---|
| 1. Staphylococcus aureus NEMC 87-69 | >128 | — | — |
| 2. Staphylococcus aureus ROSE (MP) | >128 | 8 | 16 |
| 3. Staphylococcus aureus IVES 6-542 | >128 | — | — |
| 4. Staphylococcus aureus IVES 5-160 | >128 | 4 | 8 |
| 5. Staphylococcus aureus IVES 5-396 | >128 | 4 | 8 |
| 6. Staphylococcus aureus VGH 84-47 | >128 | 8 | 8 |
| 7. Staphylococcus aureus CMC 83-131 | >128 | 16 | 32 |
| 8. Staphylococcus aureus SMITH (MP) | >128 | 4 | 4 |
| 9. Staphylococcus aureus ATCC 25923 | >128 | 8 | 32 |
| 10. Staphylococcus aureus ATCC 29213 | >128 | 16 | 16 |
| 11. Staphylococcus haemolyticus AVAH 88-1 | >128 | 32 | 32 |
| 12. Staphylococcus haemolyticus AVAH 88-3 | >128 | 16 | 16 |
| 13. Staphylococcus k 82–26 | >128 | — | — |
| 14. Staphylococcus epidermidis IVES 455 | >128 | 4 | 8 |
| 15. Staphylococcus epidermidis ATCC 12228 | >128 | — | — |
| 16. Enterococcus spp. ARUM 87-41 | >128 | 32 | 64 |
| 17. Enterococcus spp. CHBM 88-60 | >128 | 64 | 64 |
| 18. Enterococcus spp. WRVA 88-33 | >128 | 64 | 128 |
| 19. Enterococcus spp. UCI 85-30 | >128 | 32 | 64 |
| 20. Enterococcus spp. VGH 84-69 | >128 | 32 | 64 |
| 21. Enterococcus spp. CMC 83-120 | >128 | 32 | 128 |
| 22. Streptococcus pyogenes AMCH 88-84 | 4 | .12 | .5 |
| 23. Streptococcus pyogenes AMCH 88-86 | 8 | .25 | .5 |
| 24. Streptococcus pyogenes C203 (MP) | — | 1 | 2 |
| 25. Streptococcus pneumoniae CHBM 88-70 | 8 | — | — |
| 26. Streptococcus pneumoniae CHBM 88-75 | 4 | — | — |
| 27. Streptococcus pneumoniae TEX 85-2 | 16 | .5 | 2 |
| 28. Bacillus cereus DAVIES | >128 | 64 | 128 |
| 29. Klebsiella pneumoniae NEMC 87-271 | >128 | >128 | >128 |
| 30. Escherichia coli ATCC 25922 | >128 | >128 | >128 |
| 31. Escherichia coli ATCC 35218 | >128 | >128 | >128 |
| 32. Escherichia coli D-21 | >128 | — | — |
| 33. Escherichia coli D-22 | >128 | — | — |
| 34. Pseudomonas aeruginosa 12-4-4 (MP) | — | >128 | >128 |

As can be seen from the in vitro data above, LL-E19020 Epsilon and LL-E19020 Epsilon$_1$ are antibacterial agents.

EXAMPLE 13

In Vitro Antibacterial Activity Of LL-E19020 Alpha$_1$

The in vitro antibacterial activity of LL-E19020 Alpha$_1$ is determined against a spectrum of gram positive and gram negative bacteria according to the procedure described in Example 11.

IN VITRO ACTIVITY OF LL-E19020 ALPHA$_1$
MINIMAL INHIBITORY CONCENTRATION (MCG/ML)

| ORGANISM | LL-E19020-ALPHA$_1$ |
|---|---|
| 1. Staphylococcus aureus NEMC 87-69 | >32 |
| 2. Staphylococcus aureus ROSE (MP) | >32 |
| 3. Staphylococcus aureus IVES 6-542 | >32 |
| 4. Staphylococcus aureus IVES 5-160 | >32 |
| 5. Staphylococcus aureus IVES 5-396 | >32 |
| 6. Staphylococcus aureus VGH 84-47 | >32 |
| 7. Staphylococcus aureus CMC 83-131 | >32 |
| 8. Staphylococcus aureus SMITH (NP) | >32 |
| 9. Staphylococcus aureus K 82-26 | >32 |
| 10. Staphylococcus aureus ATCC 25923 | >32 |
| 11. Staphylococcus aureus ATCC 2913 | >32 |
| 12. Staphylococcus haemolyticus AVAH 88-1 | >32 |
| 13. Staphylococcus haemolyticus AVAH 88-3 | >32 |
| 14. Staphylococcus epidermidis IVES 2-455 | >32 |
| 15. Staphylococcus epidermidis ATCC 12228 | >32 |
| 16. Enterococcus spp. ARUM 87-41 | >32 |
| 17. Enterococcus spp. CHBM 88-60 | >32 |
| 18. Enterococcus spp. WRVA 88-33 | >32 |
| 19. Enterococcus spp. UCI 85-30 | >32 |
| 20. Enterococcus spp. VGH 84-69 | >32 |
| 21. Enterococcus spp. CMC 83-120 | >32 |
| 22. Streptococcus pyogenes AMCH 88-84 | 0.12 |
| 23. Streptococcus pyogenes AMCH 88-86 | 2 |
| 24. Streptococcus pneumoniae CHBM 88-75 | .5 |
| 25. Streptococcus pneumoniae CHBM 88-70 | 2 |
| 26. Streptococcus pneumoniae TEX 85-2 | 2 |
| 27. Bacillus cereus DAVIES | >32 |
| 28. Klebsiella pneumoniae NEMC 87-271 | >32 |

| IN VITRO ACTIVITY OF LL-E19020 ALPHA$_1$ MINIMAL INHIBITORY CONCENTRATION (MCG/ML) | |
|---|---|
| ORGANISM | LL-E19020-ALPHA$_1$ |
| 29. *Escherichia coli* ATCC 25922 | >32 |
| 30. *Escherichia coli* ATCC 35218 | >32 |
| 31. *Escherichia coli* D-21 | >32 |
| 32. *Escherichia coli* D-22 | >32 |

As can be seen from the in vitro data above, LL-E19020 alpha$_1$, has activity against Streptococcus.

The in vitro antibacterial activity of LL-E19020 alpha$_1$ is also determined against a spectrum of anaerobic bacteria.

| IN VITRO ACTIVITY OF LL-E19020 ALPHA$_1$ MINIMAL INHIBITORY CONCENTRATION (MCG/ML) | |
|---|---|
| ORGANISM | E 19020 Alpha$_1$ |
| 1. B.fragilis ATCC 25285 | >32 |
| 2. B.vulgatus ATCC 29327 | 8 |
| 3. B.theta ATCC 29741 | >32 |
| 4. B.theta ATCC 29742 | >32 |
| 5. C.Perf. ATCC 13124 | 1 |
| 6. C.diff. ATCC 17858 | 1 |
| 7. Ps. mag ATCC 29328 | ≧0.015 |
| 8. Ps. mag ATCC 14956 | ≦0.015 |
| 9. Ps. asarc. ATCC 29743 | ≦0.015 |

EXAMPLE 14

In Vitro Antibacterial Activity Of LL-E19020 Zeta and LL-E19020 Eta

The in vitro antibacterial activity of LL-E19020 zeta and LL-E19020 eta is determined against a spectrum of gram positive and gram negative bacteria by a standard agar dilution method as described in Example 11.

| In vitro Activity of LL-E19020 Zeta and LL-E19020 Eta MINIMAL INHIBITORY CONCENTRATION (MCG/ML) | | |
|---|---|---|
| | LL-E 19020 | |
| ORGANISM | ZETA | ETA |
| 1. Staphylococcus aureus NEMC 87-69 | >64 | >64 |
| 2. *Staphylococcus aureus* ROSE (MP) | >64 | >64 |
| 3. *Staphylococcus aureus* IVES 6-542 | >64 | >64 |
| 4. *Staphylococcus aureus* IVES 5-160 | >64 | >64 |
| 5. *Staphylococcus aureus* IVES 5-396 | >64 | >64 |
| 6. *Staphylococcus aureus* VGH 84-47 | >64 | >64 |
| 7. *Staphylococcus aureus* CMC 83-131 | >64 | >64 |
| 8. *Staphylococcus aureus* SMITH (MP) | >64 | >64 |
| 9. *Staphylococcus aureus* ATCC 25923 | >64 | >64 |
| 10. *Staphylococcus aureus* ATCC 29213 | >64 | >64 |
| 11. *Staphylococcus haemolyticus* AVAH 88-1 | >64 | >64 |
| 12. *Staphylococcus haemolyticus* AVAH 88-3 | >64 | >64 |
| 13. *Staphylococcus k* 82-26 | >64 | >64 |
| 14. *Staphylococcus epidermidis* IVES 2-455 | >64 | >64 |
| 15. *Staphylococcus epidermidis* ATCC 12228 | >64 | >64 |
| 16. *Enterococcus spp.* ARUM 87-41 | >64 | >64 |
| 17. *Enterococcus spp.* CHBM 88-60 | >64 | >64 |
| 18. *Enterococcus spp.* WRVA 88-33 | >64 | >64 |
| 19. *Enterococcus spp.* UCI 85-30 | >64 | >64 |
| 20. *Enterococcus spp.* VGH 84-69 | >64 | >64 |
| 21. *Enterococcus spp.* CMC 83-120 | >64 | >64 |
| 22. *Streptococcus pyogenes* AMCH 88-84 | 0.5 | 4 |
| 23. *Streptococcus pyogenes* AMCH 88-86 | 1 | 4 |
| 24. *Streptococcus pneumoniae* CHBM 88-70 | 1 | 4 |
| 25. *Streptococcus pneumoniae* CHBM 88-75 | 1 | 4 |
| 26. *Streptococcus pneumoniae* TEX 85-2 | 16 | 32 |
| 27. *Bacillus cereus* DAVIES | >64 | >64 |
| 28. *Klebsiella pneumoniae* NEMC 87-271 | >64 | >64 |
| 29. *Escherichia coli* ATCC 25922 | >64 | >64 |
| 30. *Escherichia coli* ATCC 35218 | >64 | >64 |
| 31. *Escherichia coli* D-21 | >64 | >64 |

| In vitro Activity of LL-E19020 Zeta and LL-E19020 Eta MINIMAL INHIBITORY CONCENTRATION (MCG/ML) | | |
|---|---|---|
| | LL-E 19020 | |
| ORGANISM | ZETA | ETA |
| 32. *Escherichia coli* D-22 | >32 | >64 |

The in vitro antibacterial activity of LL-E19020 zeta and LL-E19020 eta is also determined against a spectrum of anaerobic bacteria.

| In Vitro Activity of LL-E19020 Zeta and LL-E19020 Eta MINIMAL INHIBITORY CONCENTRATION (MCG/ML) | | |
|---|---|---|
| ORGANISM | LL-E192020 ZETA | LL-E19020 ETA |
| 1. B.fragilis ATCC 25285 | >64 | >64 |
| 2. B.vulgatus ATCC 29327 | 32 | 2 |
| 3. B.theta ATCC 29741 | >64 | >64 |
| 4. B.theta ATCC 29742 | >64 | >64 |
| 5. C.perf. ATCC 13124 | 32 | 4 |
| 6. C.diff. ATCC 17858 | 8 | 4 |
| 7. Ps. mag ATCC 29328 | 0.06 | ≧0.03 |
| 8. Ps. mag ATCC 14956 | ≧0.03 | ≧0.03 |
| 9. Ps. asarc. ATCC 29743 | ≧0.03 | ≧0.03 |

As can be seen from the in vitro data above, LL-E19020 zeta and LL-E19020 eta are antibacterial agents.

I claim:

1. A method for increasing the efficiency of food utilization by meat-producing animals which comprises orally administering to said animals a feed efficiency increasing amount of an antibiotic LL-E19020 gamma, characterized by:

(a) the structure

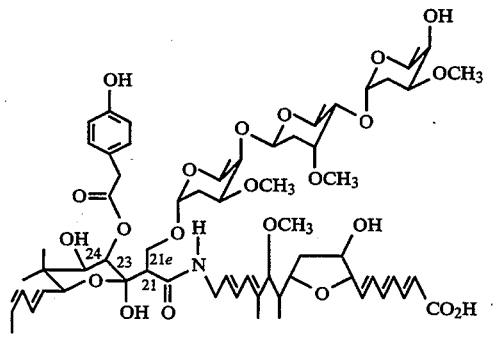

(b) an elemental analysis: C 62.22; H 7.77; N 0.92;
(c) a molecular weight of 1241 (FABMS=M/Z 1264 corresponding to [M+Na]+);
(d) a specific optical rotation: $[\alpha]_D^{26°} = -7°$ (1.001, MeOH)
(e) a characteristic ultraviolet absorption spectrum as shown in FIG. I of the attached drawings;
(f) a characteristic infrared absorption spectrum as shown in FIG. II of the attached drawings;
(g) a characteristic proton nuclear magnetic resonance spectrum as shown in FIG. III of the attached drawings;
(h) a characteristic carbon-13 nuclear magnetic resonance spectrum as shown in FIG. IV of the attached drawings;

(i) a characteristic HPLC retention time of 18.5 minutes using a gradient of acetonitrile in aqueous acetic acid; and (j) a characteristic HPLC retention time of 19.6 minutes using a gradient of dioxane in aqueous acetic acid, or a pharmacologically suitable salt thereof.

2. The method according to claim 1 wherein the antibiotic or antibiotic salt is administered in the feed or water at a concentration of about 0.001 ppm to 1.000 ppm.

3. The method according to claim 1 wherein the animals are cattle, sheep, swine, goats, horses, poultry or rabbits.

4. An animal feed composition for increasing the efficiency of food utilization in warm blooded animals comprising an edible carrier and a feed efficiency increasing amount of an antibiotic LL-E19020 gamma, characterized by:

(a) the structure

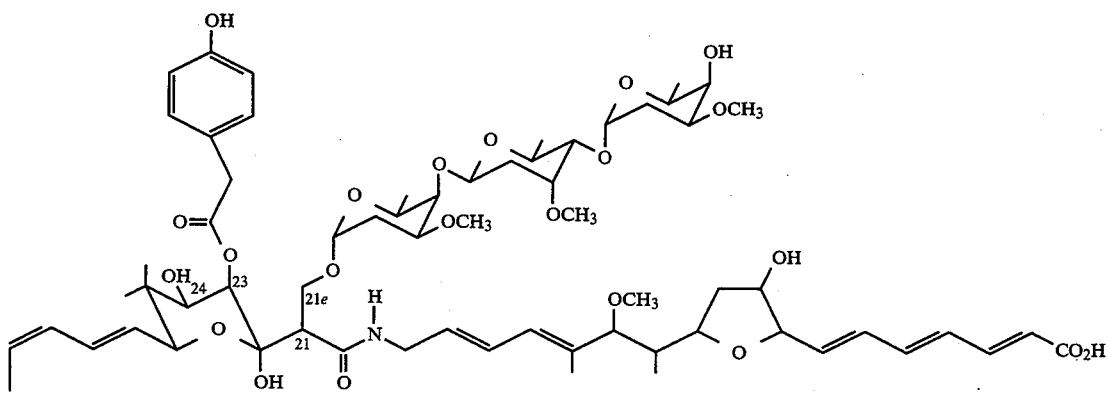

(b) an elemental analysis: C 62.22; H 7.77; N 0.92;
(c) a molecular weight of 1241 (FABMS=M/Z 1264 corresponding to [M+Na]+);
(d) a specific optical rotation: $[\alpha]_D^{26°} = -7°$ (1.001, MeOH)
(e) a characteristic ultraviolet absorption spectrum as shown in FIG. I of the attached drawings;
(f) a characteristic infrared absorption spectrum as shown in FIG. II of the attached drawings;
(g) a characteristic proton nuclear magnetic resonance spectrum as shown in FIG. III of the attached drawings;
(h) a characteristic carbon-13 nuclear magnetic resonance spectrum as shown in FIG. IV of the attached drawings;
(i) a characteristic HPLC retention time of 18.5 minutes using a gradient of acetonitrile in aqueous acetic acid; and
(j) a characteristic HPLC retention time of 19.6 minutes using a gradient of dioxane in aqueous acetic acid, or a pharmacologically suitable salt thereof.

5. The animal feed composition according to claim 4 wherein the antibiotic is present in an amount sufficient to provide a final concentration of about 0.001–1.000 ppm of antibiotic in the feed.

* * * * *